US012708311B2

(12) United States Patent
Awasthi et al.

(10) Patent No.: US 12,708,311 B2
(45) Date of Patent: Aug. 18, 2026

(54) APPARATUS AND A METHOD FOR IDENTIFYING THE PROGRESSION OF CORONARY HEART DISEASE

(71) Applicant: Anumana, Inc., Cambridge, MA (US)

(72) Inventors: Samir Awasthi, Boston, MA (US); Shashi Kant, Bengaluru (IN); Rakesh Barve, Bengaluru (IN); Shahir Asfahan, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/771,472

(22) Filed: Jul. 12, 2024

(65) Prior Publication Data

US 2026/0013775 A1 Jan. 15, 2026

(51) Int. Cl.
*A61B 5/346* (2021.01)
*A61B 5/00* (2006.01)

(52) U.S. Cl.
CPC ............ *A61B 5/346* (2021.01); *A61B 5/7267* (2013.01)

(58) Field of Classification Search
CPC .............................. A61B 5/346; A61B 5/7267
See application file for complete search history.

(56) References Cited

U.S. PATENT DOCUMENTS

2015/0182114 A1* 7/2015 Wang ..................... A61B 90/90 600/549
2020/0211713 A1* 7/2020 Shadforth ............. G16H 50/50
2020/0397324 A1* 12/2020 Paak .................... A61B 5/7275
2021/0353203 A1* 11/2021 Burman ................. G16H 50/30
2022/0392065 A1* 12/2022 Min ..................... A61B 6/5205
(Continued)

FOREIGN PATENT DOCUMENTS

CA 3216263 A1 10/2022
CN 116580845 A 8/2023
(Continued)

OTHER PUBLICATIONS

S. Yang, et al. "High-Risk Morphological and Physiological Coronary Disease Attributes as Outcome Markers After Medical Treatment and Revascularization", JACC: Cardiovascular Imaging, vol. 14, Issue 10, 2021, https://doi.org/10.1016/j.jcmg.2021.04.004 (Year: 2021).*

(Continued)

*Primary Examiner* — Amanda L Steinberg
*Assistant Examiner* — Laura Hodge
(74) *Attorney, Agent, or Firm* — CALDWELL LLC

(57) ABSTRACT

An apparatus for identifying the progression of coronary heart disease has been disclosed. The apparatus includes at least processor and a memory communicatively connected to the processor. The memory instructs the processor to receive a subject profile associated with a subject, wherein the subject profile comprises a plurality of electrocardiogram (ECG) data. The memory instructs the processor to identify contextual data as a function of the subject profile. The memory instructs the processor to generate a set of cardiac scores as function of the contextual data and the plurality of ECG data using a set of cardiac machine learning models. The memory instructs the processor to select at least one stage of coronary heart disease from a plurality of stages of coronary heart disease of the subject as a function of the set of cardiac scores.

12 Claims, 10 Drawing Sheets

(56) References Cited

U.S. PATENT DOCUMENTS

| | | | | |
|---|---|---|---|---|
| 2023/0394663 | A1* | 12/2023 | Min | A61B 5/055 |
| 2023/0419488 | A1 | 12/2023 | Min et al. | |
| 2024/0312018 | A1* | 9/2024 | Min | G06T 5/60 |
| 2024/0366158 | A1* | 11/2024 | Smith | H04L 51/02 |

FOREIGN PATENT DOCUMENTS

| | | | | |
|---|---|---|---|---|
| CN | 117637174 | A | * | 3/2024 |
| IN | 202311019558 | A | | 5/2023 |
| RU | 2008104602 | A | | 8/2009 |

OTHER PUBLICATIONS

Min JK, Chang HJ, Andreini D, Pontone G, Guglielmo M, Bax JJ, Knaapen P, Raman SV, Chazal RA, Freeman AM, Crabtree T, Earls JP. Coronary CTA plaque volume severity stages according to invasive coronary angiography and FFR. J Cardiovasc Comput Tomogr. Sep.-Oct. 2022; doi: 10.1016/j.jcct.2022.03.001 (Year: 2022).*

A. Rosendael, et al. "Percent atheroma volume: Optimal variable to report whole-heart atherosclerotic plaque burden with coronary CTA, the PARADIGM study", Journal of Cardiovascular Computed Tomography, vol. 14, Issue 5, 2020, https://doi.org/10.1016/j.jcct.2020.01.012. (Year: 2020).*

Maria Trigka, "Long-Term Coronary Artery Disease Risk Prediction with Machine Learning Models"; Published: Jan. 20, 2023.

* cited by examiner time

<

Cardiac Report
800

| | Score | Confidence Interval 140 |
|---|---|---|
| First Cardiac Score 128a | 4/100 | 3% |
| Second Cardiac Score 128b | 25/100 | 20% |
| Third Cardiac Score 128c | 67/100 | 95% |
| Fourth Cardiac Score 128d | 77/100 | 65% |

The patient's cardiac score, a significant 67 out of 100, indicates a moderate to severe level of CHD, reflecting substantial arterial blockage and reduced blood flow to the heart. Diagnostic findings have confirmed the presence of multiple atherosclerotic plaques in the coronary arteries, significantly hindering cardiac function. Based on these findings, the treatment plan recommended in the report includes the initiation of high-dose statin therapy, beta-blockers to manage chest pain and reduce myocardial oxygen demand, and possibly considering revascularization procedures such as angioplasty to restore adequate blood flow.

APPARATUS AND A METHOD FOR IDENTIFYING THE PROGRESSION OF CORONARY HEART DISEASE

FIELD OF THE INVENTION

The present invention generally relates to the field of medical technology. In particular, the present invention is directed to an apparatus and a method for identifying the progression of coronary heart disease.

BACKGROUND

Medical professionals have long struggled to track the progression of coronary heart disease without the use of invasive procedures. This process has devolved to the use of a number of medical tests along with educated guesses from a medical professional. In many cases, these tests not only require significant time and expense but also subject patients to discomfort and potential complications.

SUMMARY OF THE DISCLOSURE

In an aspect, an apparatus for the identifying the progression of coronary heart disease is disclosed. The apparatus includes at least processor and a memory communicatively connected to the processor. The memory instructs the processor to receive a subject profile associated with a subject, wherein the subject profile comprises a plurality of electrocardiogram (ECG) data. The memory instructs the processor to identify contextual data as a function of the subject profile. The memory instructs the processor to generate a set of cardiac scores as function of the contextual data and the plurality of ECG data using a set of cardiac machine learning models. The memory instructs the processor to select at least one stage of coronary heart disease from a plurality of stages of coronary heart disease of the subject as a function of the set of cardiac scores.

In another aspect, a method for the identifying the progression of coronary heart disease is disclosed. The method includes receiving, using the at least a processor, a subject profile associated with a subject, wherein the subject profile comprises a plurality of electrocardiogram (ECG) data. The method includes identifying, using the at least a processor, contextual data as a function of the subject profile. The method includes generating, using the at least a processor, a set of cardiac scores as function of the contextual data and the plurality of ECG data using a set of cardiac machine learning models. The method includes selecting, using the at least a processor, at least one stage of coronary heart disease from a plurality of stages of coronary heart disease of the subject as a function of the set of cardiac scores.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 8 is an illustration of an exemplary cardiac report;

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and a method for identifying the progression of coronary heart disease. The apparatus includes at least processor and a memory communicatively connected to the processor. The memory instructs the processor to receive a subject profile associated with a subject, wherein the subject profile comprises a plurality of electrocardiogram (ECG) data. The memory instructs the processor to identify contextual data as a function of the subject profile. The memory instructs the processor to generate a set of cardiac scores as function of the contextual data and the plurality of ECG data using a set of cardiac machine learning models. The memory instructs the processor to select at least one stage of coronary heart disease from a plurality of stages of coronary heart disease of the subject as a function of the set of cardiac scores. Exemplary embodiments illustrating aspects of the present disclosure are described below in the context of several specific examples.

Figure 1:
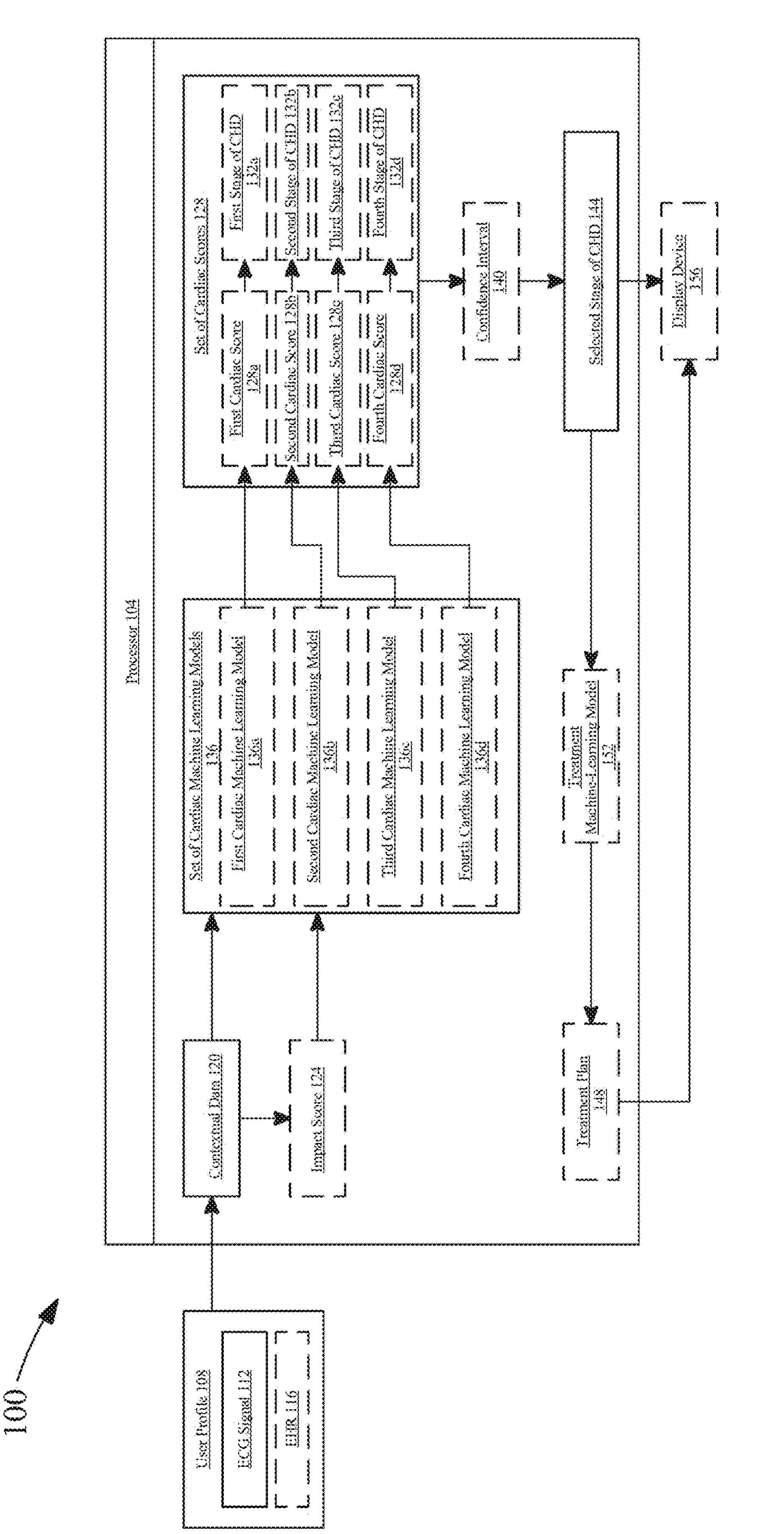
FIG. 1 is a block diagram of an exemplary embodiment of an apparatus for identifying the progression of coronary heart disease.

Referring now to FIG. 1, an exemplary embodiment of an apparatus 100 for identifying the progression of coronary heart disease is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory. Memory is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 may be configured to receive a subject profile 108 from a subject. For the purposes of this disclosure, an "subject profile" is a data structure including data about a subject. A subject profile 108 may describe personal information regarding the subject. In a non-limiting embodiment, a subject profile 108 may describe the subject's height, weight, sex, age, name, contact information, medical history, and the like. A subject profile 108 may also include testing results from various medical tests. This may include CT scans, ECGs, EKGs, Observations of a medical professional, familial history, vital signs of the subject, and the like. Subject profiles 108 may be initiated and updated by either the processor itself, the subject, a third party, electronic medical records, and the like indicating a versatile system that integrates data from multiple sources to maintain up-to-date and accurate profiles.

With continued reference to FIG. 1, processor 104 a subject profile 108 may include a plurality of electrocardiogram (ECG) data 112 from a subject. As used in the current disclosure, a "electrocardiogram data" is a signal representative of the electrical activity of the heart. The ECG data 112 may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. The ECG data 112 can be used to help diagnose various heart conditions, such as arrhythmias, myocardial infarction (heart attack), conduction abnormalities, electrolyte imbalances, coronary heart disease, and the like. In an embodiment, each sensor may generate an individual ECG data 112.

With continued reference to FIG. 1, the plurality of electrocardiogram data 112 may be generated using at least a sensor. As used in this disclosure, a "sensor" is a device that is configured to detect an input and/or a phenomenon and transmit information related to the detection. Sensor may detect a plurality of data. A plurality of data detected by sensor may include, but is not limited to, electrocardiogram data 112, heart rate, blood pressure, electrical signals related to the heart, and the like. In one or more embodiments, and without limitation, sensor may include a plurality of sensors. At least a sensor may include an ECG machine. In one or more embodiments, and without limitation, sensor may include one or more electrodes, and the like. Electrodes used for an electrocardiogram (ECG) are small sensors or conductive patches that are placed on specific locations on the body to detect and record the electrical signals generated by the heart. Senor serves as the interface between the body and the ECG machine, allowing for the measurement and recording of the heart's electrical activity. A plurality of sensors may include 10 electrodes used for a standard 12-lead ECG, placed in specific positions on the chest and limbs of the patient. Sensors may also include various lead systems including, 1-lead, 2-lead, 6-leads, 12, leads, standard limb leads, augmented limb leads, pectoral leads, and the like. These electrodes are typically made of a conductive material, such as metal or carbon, and are connected to lead wires that transmit the electrical signals to the ECG machine for recording. Proper electrode placement may be crucial to ensure accurate signal detection and recording. A number of electrodes used by an ECG machine may depend on a particular machine in use and may vary from a single electrode on a wearable device to twelve or more electrodes, or any number in between.

With continued reference to FIG. 1, the plurality of sensors may be placed on each limb, wherein there may be at least one sensor on each arm and/or leg of the subject. These sensors may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line.

With continued reference to FIG. 1, the plurality of sensors may include augmented unipolar sensors. These sensors may be labeled as aVR, aVL, and aVF. These sensor may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions.

With continued reference to FIG. 1, processor 104 may be configured to receive subject profile 108 from an electronic health records (EHR) 116. As used in the current disclosure, "electronic health record" is a data structure which includes a collection of a health data associated with the subject. As used in the current disclosure, "health data" refers to the collection of information related to a patient's health and healthcare. Health data may include elements of data regarding treatment records, medical history, laboratory results, radiology reports, medical records, clinical notes, and the like. An electronic health record (EHR) 116 may be a digital version of a patient's medical information that is stored and managed in a computerized system. It may be a comprehensive, longitudinal collection of a patient's health-related data that includes medical history, diagnoses, medications, treatment plans, test results, and other relevant health information. EHRs 116 may contain a wide range of patient information, including personal demographics, medical history, allergies, immunizations, medications, laboratory results, imaging reports, surgical procedures, and progress notes. This comprehensive data may provide a complete overview of a patient's health and facilitates informed decision-making. EHRs 116 may include a patient's past and current medical conditions, surgeries, allergies, immunization records, medications, symptoms, medical observations, and any significant health events. EHRs 116 may additionally include a large amount of information regarding the patient's health background. This may include previous diagnosis, medical tests, medical imaging, and the like. EHRs may include documentation, observations, assessments, and treatment plans from medical professionals. This may include progress notes, discharge summaries, and other relevant clinical documentation. EHRs may include information related to prescribed medications, including dosage, frequency, symptoms, effect, and duration. EHRs may include test results, which may include laboratory test results, radiology reports, medical imaging reports, and other diagnostic imaging findings.

With continued reference to FIG. 1, EHRs 116 may be received by processor 104 via user input. For example, and without limitation, the user or a third party may manually input EHRs 116 using a graphical user interface of processor 104 or a remote device, such as for example, a smartphone or laptop. EHRs 116 may additionally be generated via the answer to a series of questions. In a non-limiting embodiment, a user may be prompted to input specific information or may fill out a questionnaire. In an embodiment, a graphical user interface may display a series of questions to prompt a user for information pertaining to the EHRs 116. The EHRs 116 may be transmitted to processor 104, such as via a wired or wireless communication, as previously discussed in this disclosure.

With continued reference to FIG. 1, plurality of EHRs 116 may include a plurality of metadata. As used in the current disclosure, "metadata" refers to descriptive information or attributes that provide context, structure, and meaning to data. Metadata is essentially data about data. Metadata may help in understanding and managing various aspects of data, such as its origin, content, format, quality, and usage. It may play a crucial role in organizing, searching, and interpreting data effectively. Metadata may include descriptive metadata, structural metadata, administrative metadata, technical metadata, provenance metadata, usage metadata, and the like. Metadata may be organized and managed through metadata schemas, standards, or frameworks. These provide guidelines and specifications for capturing, storing, and exchanging metadata in a consistent and structured manner. Common metadata standards include Dublin Core, Metadata Object Description Schema (MODS), and the Federal Geographic Data Committee (FGDC) metadata standard. In some cases, metadata may be associated with textual data or image data. In some cases, metadata may include data associated with the health of the patient and the patient's medical records. Metadata includes patient-specific information such as unique identifiers (e.g., medical record number, national identification number), patient demographics (name, date of birth, gender), contact details, and emergency contact information. These identifiers help in linking and identifying the EHR of individual patients. Each entry or update in an EHR may be accompanied by a date and time stamp. This metadata may be captured when the event or documentation took place, allowing processor 104 to track the chronological order of patient encounters, treatments, test results, and other relevant information. Metadata may include details about the healthcare professional or user who created or updated a specific EHR entry. This information may include the name, credentials, role, and department of the author. It helps in accountability, audit trails, and ensuring data integrity. Metadata may indicate the source of the EHR data, whether it was entered directly by a healthcare provider, imported from a laboratory or diagnostic system, received from external healthcare organizations, or captured through patient-generated sources (e.g., wearables, patient-reported data). Metadata may include information regarding access permissions, user roles, and security settings associated with the EHR 116. This metadata may be used to enforce privacy and security protocols, ensuring that only authorized individuals can view, modify, or access specific portions of the EHR. Metadata may contain notes, comments, or observations made by a medical professional. These annotations might highlight specific features, anomalies, or noteworthy aspects of the EHR. The date and time when the slide was prepared, analyzed, or labeled can be associated as metadata.

With continued reference to FIG. 1, the EHR 116 may include a plurality of multi-modal data associated with a subject. As used in the current disclosure, "multi-modal data" is data which includes a plurality of modalities data. Modalities of data may include images, text, audio, documents, electronic health records, sensor data, and the like. Multi-modal data may include textual data. As used in the current disclosure, "textual data" is a collection of data that consists of text-based information. Textual data may include any written information, such as documents, emails, notes, handwriting, chat conversations, and the like. Examples of textual data may include documents, captions, sentences, paragraphs, free-text fields, transcriptions, prognostic labels, and the like. Textual data may include data from a plurality of digital or handwritten notes. Notes may be written by a medical professional. The notes may depict conditions of the patient. Textual data may be associated with electronic health records (EHRs). Textual data may refer to the written or typed information that is recorded and stored as part of a patient's health record in a digital format. It includes a wide range of textual information that provides details about the patient's medical history, diagnoses, treatments, procedures, medications, observations, clinical notes, and other relevant healthcare information. Multi-modal data may include image data. As used in the current disclosure, "image data" is a collection of data that consists of data associated with a plurality of images. Image data encompasses visual representations captured through cameras or generated through medical imaging, graphs, microscopes, or other image capturing systems. Image data associated with electronic health records (EHRs) refers to the visual information that is linked or integrated with the patient's health record. It includes medical images such as X-rays, CT scans, MRI scans, ultrasound images, endoscopy images, pathology slides, and other types of diagnostic or clinical images.

With continued reference to FIG. 1, processor 104 may be configured to receive a subject profile 108 or an EHR 116 using an application programming interface (API). As used herein, an "application programming interface" is a set of functions that allow applications to access data and interact with external software components, operating systems, or microdevices, such as another web application or computing device. An API may define the methods and data formats that applications can use to request and exchange information. APIs enable seamless integration and functionality between different systems, applications, or platforms. An API may deliver subject profile 108 or an EHR 116 to apparatus 100 from a system/application that is associated with a subject, medical provider, or other third-party custodian of subject information. In an embodiment, an API may be configured to query for web applications or other websites to retrieve a subject profile 108 or an EHR 116. An API may be further configured to filter through web applications according to a filter criterion. In this disclosure, "filter criteria" are conditions the web applications must fulfill in order to qualify for API. Web applications may be filtered based off these filter criteria. Filter criterion may include, without limitation, web application dates, web application traffic, web application types, web applications addresses, and the like. Once an API filters through web applications according to a filter criterion, it may select a web application. Processor 104 may transmit, through the API, ECG data 112 to apparatus 100. API may further automatically fill out user entry fields of the web application with the user credentials in order to gain access to the ECG data 112. Web applications may include, without limitation, a medical database, hospital website, file scanning, email programs, third party websites, governmental websites, or the like.

With continued reference to FIG. 1, subject profile 108 and/or EHR 116 may be received from a user using a chatbot. A chatbot can be used to receive inputs from a user to generate subject data, wherein a chatbot input is discussed in greater detail herein below. The chatbot may be configured to ask a user a plurality of inquiries related to one or more aspects of their business. The chatbot may use natural language processing techniques to understand and extract key information from the user's responses. This may help in determining the specific symptoms and/or medical conditions of the subject. In a non-limiting example, a chatbot may be used to gather information regarding the subject's family medical history or the subject medical history. In some cases, a chatbot may be used to gather more information related to the subject's current symptoms. A chatbot may present the user with inquiries regarding duration or severity of the subject's symptoms. In some cases, the collected data and user inputs may be used to generate a structured subject profile 108. Processor 104 may organize the information into different sections or categories based on the nature of the entity. This may be done using a chatbot as described herein below in FIG. 7.

With continued reference to FIG. 1, a subject profile 108 and/or EHR 116 may be generated from one or more medical records. As used in the current disclosure, a "medical record" is a document that contains information regarding the subject's medical history. Medical records may include data about any medical procedures, medical tests, medical images, observations of a medical professional, prescription history, diagnostic history, government records (i.e., birth certificates, social security cards, and the like), and the like of the subject. Medical records may be identified using a web crawler. Medical records may include a variety of types of "notes" entered over time by a medical professional. Medical records may be converted into machine-encoded text using an optical character reader (OCR).

Still referring to FIG. 1, in some embodiments, optical character recognition or optical character reader (OCR) includes automatic conversion of images of written (e.g., typed, handwritten, or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases, OCR may be an "offline" process, which analyses a static document or image frame. In some cases, handwriting movement analysis can be used as input for handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image components. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to the image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from the background of the image component. In some cases, binarization may be required for example if an employed OCR algorithm only works on binary images. In some cases, a line removal process may include the removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify a script allowing an appropriate OCR algorithm to be selected. In some cases, a character isolation or "segmentation" process may separate signal characters, for example, character-based OCR algorithms. In some cases, a normalization process may normalize the aspect ratio and/or scale of the image component.

Still referring to FIG. 1, in some embodiments, an OCR process will include an OCR algorithm. Exemplary OCR algorithms include matrix-matching process and/or feature extraction processes. Matrix matching may involve comparing an image to a stored glyph on a pixel-by-pixel basis. In some cases, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at the same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted features can be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 5-7. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. The second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2, 4, and 5.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, a subject profile 108 and/or EHR 116 may be generated using a web crawler. A "web crawler," as used herein, is a program that systematically browses the internet for the purpose of web indexing. The web crawler may be seeded with platform URLs, wherein the crawler may then visit the next related URL, retrieve the content, index the content, and/or measures the relevance of the content to the topic of interest. In some embodiments, processor 104 may generate a web crawler to compile the subject profile 108 and/or EHR 116. The web crawler may be seeded and/or trained with a reputable website, such as the subject's business website, to begin the search. A web crawler may be generated by a processor 104. In some embodiments, the web crawler may be trained with information received from a user through a user interface. In some embodiments, the web crawler may be configured to generate a web query. A web query may include search criteria received from a user. For example, a user may submit a plurality of websites for the web crawler to search to extract data related to the subject profile 108, past subject profiles 108, EHRs 116, based on criteria such as a time, location, and the like. In some cases, a web crawler may be seeded with the website to the entities website. The process of seeding a web crawler refers to the process of providing an initial set of URLs or starting points from which the crawler begins its exploration of the web. These initial URLs are often called seed URLs or a seed set. Seeding may be a curtail step in the web crawling process as it defines the starting point for discovering and indexing web pages.

With continued reference to FIG. 1, processor 104 may identify contextual data 120 as a function of the subject profile 108. As used in the current disclosure, "contextual data" refers to details about the subject that provide a more comprehensive understanding of the ECG data 112. Contextual data 120 associated with the subject profile 108 may be information that surrounds and gives meaning to that data. This additional information may assist the apparatus 100 in interpreting and comprehending the ECG data 112. The use of contextual data 120 may provide a more individualized healthcare diagnosis. By accounting for the personal and medical nuances of each subject, the system may facilitate a deeper and more accurate understanding of heart health, directly influencing the precision of diagnostics. These patient-specific factors can influence the interpretation of ECG readings and the subsequent diagnosis. In an embodiment, contextual data 120 may include the patient's medical history, presenting symptoms, risk factors for CHD, and any previous cardiac events or procedures. Medical history that is particularly relevant includes conditions like diabetes, hypertension, hyperlipidemia, heart disease, family history, all of which increase the likelihood of CHD. Additionally, symptoms such as chest pain, shortness of breath, and episodes of syncope or palpitations can provide critical clues that guide the interpretation of the ECG. For instance, certain patterns of chest pain might suggest ischemia, which could correlate with specific changes in the ECG like ST-segment elevations or depressions. The patient's age and sex also play a significant role, as ECG norms can vary across different demographics, and the pattern of heart disease may present differently. Risk factors such as smoking, obesity, and a sedentary lifestyle further contribute to the overall assessment and interpretation of the ECG. The presence of these risk factors in conjunction with ECG abnormalities may strengthen the suspicion of CHD. Previous ECGs, if available, are invaluable as they provide a baseline for comparison, helping to identify new changes that may indicate acute coronary events or progression of disease.

With continued reference to FIG. 1, processor 104 may identify contextual data 120 from a subject profile 108. Processor 104 may access the subject profile 108, which may include a wide range of information such as demographic details, medical history, current and past medical conditions, lifestyle choices, genetic data, and previous health assessments. Utilizing algorithms designed for data extraction and interpretation, the processor may scan through this information to highlight relevant data points that are crucial for assessing the subject's health status. This might involve categorizing data into different health-related themes such as cardiovascular risk factors, chronic conditions, or lifestyle habits. The processor may then apply predefined rules or machine learning models to analyze and prioritize this data based on its relevance and impact on the subject's health. For example, it might flag high blood pressure and family history of heart disease as significant risk factors for coronary heart disease. This contextual information may then be organized and made readily accessible for further analysis or to inform decision-making processes.

With continued reference to FIG. 1, the identification of contextual data 120 may include analyzing and interpreting textual data or other data elements associated with a subject profile. Processor 104 may identify textual data or other data elements associated with a subject profile 108 using natural language processing (NLP) techniques, such as tokenization, part-of-speech tagging, and named entity recognition (NER), may be employed to understand the structure, and meaning of the text.

With continued reference to FIG. 1, identifying contextual data 120 within the at least a subject profile 108 may include generating a plurality of named entities and/or keyword sets associated with the subject profile 108 using a natural language processing model. As used in the current disclosure, a "natural language processing (NLP) model" is a computational model designed to process and understand human language. It leverages techniques from machine learning, linguistics, and computer science to enable computers to comprehend, interpret, and generate natural language text. The NLP model may preprocess the textual data, wherein the input text may include all text contained within the subject profile 108, or any other data mentioned herein. Preprocessing the input text may involve tasks like tokenization (splitting text into individual words or sub-word units), normalizing the text (lowercasing, removing punctuation, etc.), and encoding the text into a numerical representation suitable for the model. The NLP model may include transformer architecture, wherein the transformers may be deep learning models that employ attention mechanisms to capture the relationships between words or sub-word units in a text sequence. They consist of multiple layers of self-attention and feed-forward neural networks. The NLP model may weigh the importance of different words or sub-word units within a text sequence while considering the context. It may enable the model to capture dependencies and relationships between words, considering both local and global contexts. This process may be used to identify a plurality of named entities.

With continued reference to FIG. 1, a language processing model may include a named entity recognition system to produce associations between one or more significant terms extracted from the subject profile 108 and detect associations, including without limitation mathematical associations, between such significant terms. Associations between language elements, where language elements include for purposes herein extracted significant terms, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted significant term indicates a given category of semantic meaning. As a further example, statistical correlations and/or mathematical associations may include probabilistic formulas or relationships indicating a positive and/or negative association between at least an extracted significant term and/or a given semantic relationship; positive or negative indication may include an indication that a given document is or is not indicating a category semantic relationship. Whether a phrase, sentence, word, or other textual element in the subject profile 108 constitutes a positive or negative indicator may be determined, in an embodiment, by mathematical associations between detected significant terms, comparisons to phrases and/or words indicating positive and/or negative indicators that are stored in memory at processor 104, or the like.

With continued reference to FIG. 1, processor 104 may employ a natural language processing (NLP) to identify keyword sets within the subject profile 108. As used in the current disclosure, a "keyword set" is a collection of relevant words or phrases selected to represent subject profile 108. This keyword set may be derived from analyzing the textual content of the subject profile 108, or any other related data that outlines what the task entails and what is needed to complete it. These keyword sets may be identified as a function of tokenizing subject profile 108, discussed in greater detail here below. A keyword set associated with contextual data 120 may encompasses terms like "Smoking," "Alcohol Consumption," "Drug Consumption," "Exercise," "Diet," "Stress," "Occupation," "Obesity," "Family History," "Diabetes," "Age and Gender," "Chest Pain," "Diabetes," and the like.

With continued reference to FIG. 1, an NLP may tokenize text within the subject profile 108 to identity keyword sets and/or named entities. This may be done by breaking down the text into smaller units or 'tokens'. In this process, a sentence or a phrase is segmented into words, phrases, symbols, or other meaningful elements that serve as the basic building blocks for analysis. For example, in the sentence "The patient has a physically fit appearance and abstains from illegal drug and alcohol consumption." Tokenization may divide this into individual keyword sets like "illegal drug," "alcohol," "physically fit appearance," and the like. This may allow processor 104 to analyze and understand the text at a more granular level, identifying and processing each token separately. In an embodiment, processor 104 may employ one or more artificial intelligence algorithms to identify and analyze the tokenized text. In an embodiment, at least a portion of the tokens that are identified by the NLP may be considered keyword sets. Identifying keyword sets from tokenized textual data may involve processing and analyzing the text to extract meaningful and relevant keywords. Once the text is tokenized, various techniques may be applied to identify keyword sets. These techniques may include frequency analysis, where frequently occurring tokens are considered potential keywords, or more sophisticated methods like natural language processing (NLP) techniques that analyze the context, semantic meaning, and relationships between tokens. In a non-limiting example, tokenization could separate a sentence into keywords and phrases like "illegal drug," "alcohol," "physically fit appearance," which are then analyzed to determine their relevance and categorization into keyword sets. The NLP system may utilize artificial intelligence algorithms to further refine the analysis, ensuring that the identified keyword sets are pertinent and comprehensive, covering terms related to the domain of interest.

With continued reference to FIG. 1, processor 104 may identify contextual data 120 within the at least a subject profile 108 using a named entity recognition (NER) system. As used in the current disclosure, a "named entity recognition (NER) system" is software that identifies a plurality of named entities from textual data. A NER system may be configured to identify a plurality of named entities from the at least a subject profile 108. A named entity refers to specific information that is automatically recognized and categorized within text. These entities typically include proper nouns such as names of conditions, symptoms, or measurements, as well as other identifiable data like dates, times, medical testing results, and the like. Named Entity Recognition (NER) is the NLP task dedicated to identifying and classifying these pieces of data into predefined categories. For example, in the sentence "The patient is experiencing shortness of breath and appears to be morbidly obese," a NER system would identify "shortness of breath" as a symptom and "morbid obesity" as a condition. The ability to accurately detect named entities is crucial in various applications, such as information retrieval, content classification, customer support automation, and more, enabling more efficient data processing and richer insights into textual content. Inputs of a NER system may include a subject profile 108, medical records, EHRs and the like. The output of a named entity recognition system may include a plurality of named entities associated with subject profile 108.

With continued reference to FIG. 1, processor 104 may employ a NER system to identify and classify tokenized text. A Named Entity Recognition (NER) system may classify tokens into predefined categories by analyzing the text data to identify and categorize specific entities according to their relevance and meaning. This process may involve parsing the text to detect patterns and contextual clues that suggest the category to which a token belongs. Categories may be related to various elements contextual data 120. Apparatus 100 may employ machine learning algorithms, which may be trained on large datasets annotated with examples of named entities, to learn the characteristics that typically define each category. By evaluating these features in the context of surrounding words and applying learned models, the NER system can accurately assign each token to its appropriate category, enabling the structured extraction of information from unstructured text data.

With continued reference to FIG. 1, processor 104 may generate contextual data 120 using a contextual machine-learning model. As used in the current disclosure, a "contextual machine-learning model" is a machine-learning model that is configured to generate contextual data 120. Contextual machine-learning model may be consistent with the machine-learning model described below in FIG. 2. Inputs to the contextual machine-learning model may include subject profiles 108, EHRs 116, examples of contextual data 120, and the like. Outputs to the contextual machine-learning model may include contextual data 120 tailored to the subject profile 108. Contextual training data may include a plurality of data entries containing a plurality of inputs that are correlated to a plurality of outputs for training a processor by a machine-learning process. In an embodiment, contextual training data may include a plurality of subject profile 108 correlated to examples of contextual data 120. Contextual training data may be received from database 300. Contextual training data may contain information about subject profiles 108, EHRs 116, examples of contextual data 120, and the like. In an embodiment, contextual training data may be iteratively updated as a function of the input and output results of past contextual machine-learning model or any other machine-learning model mentioned throughout this disclosure. Iteratively updating the contextual machine learning model may adjust the connection and weights between nodes in adjacent layers of the neural network to produce the desired values at the output nodes. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, processor may generate an impact score 124 as a function of the contextual data 120. As used in the current disclosure, an "impact score" is a quantitative measure designed to assess and convey the significance or potential severity of a patient's symptoms or medical conditions on their heart health. The impact score enables apparatus 100 to focus on the aspects of the patient's health that are most likely to influence their immediate and long-term heart health in terms of CHD. In a non-limiting example, a patient has multiple symptoms or conditions, the impact score 124 can help identify which symptoms or conditions will serve as exacerbating/mediating factors for heart disease. Each component of the patient's contextual data, whether it be a symptom like chest pain or a condition like diabetes, may be assigned its own impact score. These individual scores are then synthesized to form a composite impact score 124. This aggregation enables apparatus 100 to identify more than just the isolated risks, but also how various factors interact and compound, potentially identifying which conditions should be targeted first in treatment plans to mitigate the overall risk to heart health. In some cases, each score of the plurality of scores may be evaluated to generate a single impact score 124 to quantify the severity of the contextual data 120 surrounding the subjects heart health. For example, a patient may present with high blood pressure, elevated cholesterol levels, and a smoking habit. Each of these factors individually contributes to the risk of CHD, but their combined effect might pose a significantly higher threat. The impact score helps to aggregate and quantify this risk, providing a numerical value that reflects the total potential impact on the patient's heart health. The impact score maybe derived from the contextual data 120 gathered about the patient, which includes detailed personal and medical information such as size, gender, medical history, and symptoms. By calculating this score, the system quantifies how a specific symptom or condition could affect the patient's health evaluation, providing a standardized metric that helps in interpreting the urgency and potential impact of medical findings.

With continued reference to FIG. 1, generating an impact score may involve collecting data related to a patient's health. This data may include contextual data 120 such as medical history, symptoms, lifestyle factors, genetic information, and existing health conditions, all pertinent to assessing the risk for a specific disease such as coronary heart disease. Each element of this data may be evaluated to determine its influence on the patient's health risk. Important factors, such as high blood pressure, cholesterol levels, and smoking, may be identified and each is assigned a weight based on its demonstrated impact on heart health, derived from clinical studies and expert opinions. Individual scores may be calculated for each risk factor, taking into account their weighted significance and the severity of the patient's condition concerning each factor. These individual scores may be integrated using mathematical or statistical models, which may involve methods such as summation or averaging, or more complex algorithms that account for interactions between different factors. The resulting composite impact score is then normalized or scaled, often on a scale from 0 to 100, to facilitate its practical application for use within a machine learning model. In an embodiment, to ensure accuracy and reliability, the impact score may undergo a validation against historical data, verifying its effectiveness in predicting clinical outcomes. This validation may be valuable for assessing the model's predictive power and ensuring it can reliably inform clinical decisions. Once validated, the impact score may be implemented into the cardiac machine learning model.

With continued reference to FIG. 1, an impact score 124 may be normalized. This may be done to bring all symptoms, health conditions, genomic traits, and the like onto a comparable scale. This step is important to eliminate any bias introduced by different units or measurement scales. Normalization techniques can include min-max scaling, z-score normalization, or logarithmic transformation. In an embodiment, an impact score 124 may be expressed as a numerical score, a linguistic value, or an alphabetical score. A non-limiting example, of a numerical score, may include a scale from 0-1, 1-10, 1-100, 1-1000, and the like, wherein a rating of 1 may represent a symptom/condition with little to no impact on the subject's heart health, whereas a rating of 10 may represent a symptom/condition that has a significant impact on the subject' heart health. In another non-limiting example, linguistic values may include, "No Impact," "Moderate Impact," "Significant Impact," and the like. An impact score 124 may also quantify if the impact of the subject's heart health is positive or negative. This may be represented using a negative value in conjunction with positive values. In some embodiments, linguistic values may correspond to a linguistic variable score range. For example, a condition/symptom that receives a score between 40-60, on a scale from 1-100, may be considered a "Moderate Impact."

With continued reference to FIG. 1, processor 104 may generate an impact score 124 using an impact machine-learning model. As used in the current disclosure, an "impact machine-learning model" is a machine-learning model that is configured to generate an impact score 124. impact machine-learning model may be consistent with the machine-learning model described below in FIG. 2. Inputs to the impact machine-learning model may include contextual data 120, subject profile 108, EHR 116, examples of impact score 124, and the like. Outputs to the impact machine-learning model may include impact score 124 tailored to the contextual data 120. impact training data may include a plurality of data entries containing a plurality of inputs that are correlated to a plurality of outputs for training a processor by a machine-learning process. In an embodiment, impact training data may include a plurality of contextual data 120 correlated to examples of impact score 124. impact training data may be received from database 300. impact training data may contain information about contextual data 120, subject profile 108, EHR 116, examples of impact score 124, and the like. In an embodiment, impact training data may be iteratively updated as a function of the input and output results of past impact machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, processor 104 generates a set of cardiac scores 128 as function of the contextual data 120 and the plurality of ECG data 112. As used in the current disclosure, a "cardiac score" is a quantification of one or more factors indicative of the stage of CHD. In an embodiment, a cardiac score 128 may be a direct indicator of the amount of calcium in the coronary arteries, which is a measure of the extent of atherosclerotic plaque buildup. A cardiac score utilizes a multifaceted approach by analyzing the patient's personal and medical history (contextual data), including risk factors such as age, gender, family history of heart disease, smoking status, cholesterol levels, and other relevant health conditions like diabetes or hypertension. Additionally, it may incorporate data derived from the ECG, which might include findings like ST-segment changes, T-wave abnormalities, or evidence of previous myocardial infarctions. The cardiac score 128 may be computed using an algorithm that assigns weights to various risk factors and ECG findings based on their association with CHD. For instance, significant ECG changes might carry more weight if the patient also has multiple lifestyle risk factors. The result is a cardiac score 128 that categorizes the severity of CHD, ranging from low to high risk. This score may be used to aid healthcare providers in determining the necessity and urgency of interventions, such as lifestyle modification, medication, or more invasive procedures like angioplasty or bypass surgery. Moreover, a cardiac score may allow for dynamic monitoring over time, providing a quantitative method to assess the effectiveness of treatment strategies and adjust them as needed to optimize patient outcomes. This holistic approach ensures that the cardiac score is not just a static measurement but a dynamic tool integral to managing and mitigating CHD risk. In an embodiment, a cardiac score 128 may be expressed as a numerical score, a linguistic value, or an alphabetical score. A non-limiting example, of a numerical score, may include a scale from 0-1, 1-10, 1-100, 1-1000, and the like, wherein a score of 1 may represent subject with little to no plaque buildup, whereas a score of 10 may represent subject with significant plaque buildup. In another non-limiting example, linguistic values may include, "No plaque," "Low Plaque," "Moderate Plaque," "Severe Plaque," and the like. In some embodiments, linguistic values may correspond to a linguistic variable score range. For example, a subject that receives a score between 40-60, on a scale from 1-100, may be considered a "Moderate Plaque." The numerical score may be directly correlated to a range of total plaque volume (TPV) or percent arterial volume (PAV) of the subject.

With continued reference to FIG. 1, processor 104 may generate a cardiac scores 128 from Electrocardiogram (ECG) data 112. The ECG may be analyzed to identify key parameters such as heart rate, rhythm, and the morphology of specific waves like the P wave, QRS complex, and T wave. Abnormalities such as arrhythmias, signs of ischemia like ST-segment depression, and indications of conditions like Left Ventricular Hypertrophy (LVH) may also be carefully evaluated. Each of these abnormalities may be quantitatively assessed, with severity scores assigned based on clinical guidelines that link these ECG features with cardiovascular risk. As used in the current disclosure, a "severity score" is a quantitative measure used to evaluate the extent or intensity of abnormalities detected in the ECG waveform that are indicative of underlying cardiac conditions. This score helps clinicians gauge the urgency and potential risk associated with these abnormalities, assisting in clinical decision-making and patient management. A severity score may provide a standardized method to assess and communicate the clinical significance of various ECG findings. These might include deviations in the ST segment, T-wave inversions, signs of left or right ventricular hypertrophy, arrhythmias, and other indicators of cardiac dysfunction or myocardial ischemia. Severity scores from ECG signals may be generated by quantitatively assessing the abnormalities detected in the ECG waveform against established clinical criteria and benchmarks. Contextual data 120 may be used to identify clinical criteria and benchmarks that are appropriate for each subject based on genomic and demographic factors. Each notable deviation from the normal ECG pattern—such as ST segment elevations or depressions, T-wave inversions, arrhythmic events, and signs of ventricular hypertrophy—may be assigned a severity score based on its clinical significance and potential impact on the patient's health. These scores may reflect the urgency and severity of cardiac conditions, with higher scores typically indicating more severe abnormalities that may require immediate intervention. The individual scores for each abnormality are then combined to form an overall severity score, which provides a comprehensive measure of cardiac risk or dysfunction at the time of the ECG. These severity scores may then be integrated with contextual data from the patient's medical history—factors like age, cholesterol levels, and existing conditions like hypertension and diabetes—to generate a cardiac score 128. This integration uses a sophisticated algorithm, often incorporating weighted sums or statistical models, to calculate a composite cardiac score.

With continued reference to FIG. 1, the set of cardiac scores 128 may comprise at least one cardiac score associated with each stage of coronary heart disease of the plurality of stages of coronary heart disease. As used in the current disclosure, a "stage of coronary heart disease" refers to the progression through distinct stages, each reflecting a different level of severity. Stages of coronary heart disease 132 may include a first stage of coronary heart disease 132*a*, second stage of coronary heart disease 132*b*, third stage of coronary heart disease 132*c*, fourth stage of coronary heart disease 132*d*, up to an nth stage of coronary heart disease 132*n*. Stages of coronary heart disease 132 may be defined based on range of total plaque volume (TPV) or percent arterial volume (PAV) of the subject. The stages of Coronary Heart Disease 132 can be defined based on quantitative measurements of the total plaque volume (TPV) or the percent arterial volume (PAV) within a patient's coronary arteries. For instance, an early stage of CHD might be characterized by a lower TPV or PAV, indicating minimal plaque accumulation that has not yet significantly obstructed coronary blood flow. As the disease progresses, these volumes increase, moving a patient into more advanced stages. A moderate stage may be defined by a TPV or PAV range that shows noticeable plaque build-up, causing some reduction in blood flow but not yet leading to frequent symptoms. In severe stages, very high TPV or PAV indicates extensive plaque that significantly narrows the arteries, likely leading to symptoms such as stable angina or acute coronary syndromes. In a non-limiting example, a first stage of coronary heart disease 132*a* may be associated with TPV ($mm^3$) of 0 and/or PAV % of 0. The first stage of coronary heart disease 132*a* may be associated with a subject that has no plaque. In an additional non-limiting example, a second stage of coronary heart disease 132*b* may be associated with TPV ($mm^3$) of 0-250 and/or PAV of 0-5%. The second stage of coronary heart disease 132*b* may be associated with a subject that has mild plaque. In an additional example, a third stage of coronary heart disease 132*c* may be associated with TPV ($mm^3$) of 250-750 and/or PAV of 5-15%. The third stage of coronary heart disease 132*c* may be associated with a subject that has moderate plaque. In an additional example, a fourth stage of coronary heart disease 132*d* may be associated with TPV ($mm^3$) of greater than 750 and/or PAV of greater than 15%. The fourth stage of coronary heart disease 132*d* may be associated with a subject that has severe plaque. Each cardiac score within the set of cardiac scores 128 may be associated with at least one stage of coronary heart disease 132. In an embodiment, a set of cardiac scores 128 may include a first cardiac score 128*a* associated with a first stage of coronary heart disease 132*a*, a second cardiac score 128*b* associated with a second stage of coronary heart disease 132*b*, a third cardiac score 128*c* associated with a third stage of coronary heart disease 132*c*, a fourth cardiac score 128*d* associated with a fourth stage of coronary heart disease 132*d*, up to an nth cardiac score 128*n* associated with an nth stage of coronary heart disease 132*n*.

With continued reference to FIG. 1, in some embodiments, cardiac scores 128 may include one or more of a coronary artery calcium score, a total plaque volume, a cardiac stress test score, a propensity to test positive on a cardiac stress test, a regional wall motion abnormality, percent obstruction, probability of proximal obstruction, and the like.

With continued reference to FIG. 1, processor 104 may generate cardiac scores 128 using a set of cardiac machine-learning model 136. As used in the current disclosure, a "cardiac machine-learning model" is a machine-learning model that is configured to generate cardiac scores 128. A set of cardiac machine-learning models 136 may be consistent with the machine-learning model described below in FIG. 2. Inputs to the cardiac machine-learning model 136 may include contextual data 120, subject profile 108, EHR 116, impact score 124, ECG data 112, severity scores, examples of cardiac scores 128, and the like. Outputs to the cardiac machine-learning model 136 may include cardiac scores 128 tailored to the contextual data 120 and ECG data 112. Cardiac training data may include a plurality of data entries containing a plurality of inputs that are correlated to a plurality of outputs for training a processor by a machine-learning process. In an embodiment, cardiac training data may include a plurality of contextual data 120 and ECG data 112 correlated to examples of cardiac scores 128. Cardiac training data may be received from database 300. Cardiac training data may contain information about contextual data 120, subject profile 108, EHR 116, impact score 124, ECG data 112, severity scores, examples of cardiac scores 128, and the like. In an embodiment, cardiac training data may be iteratively updated as a function of the input and output results of past cardiac machine-learning model 136 or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, a set of cardiac machine-learning models 136*a-d* may include at least one cardiac machine learning model 136 associated with each stage of coronary heart disease 132 of the plurality of stages of coronary heart disease 132*a-d*. A set of cardiac machine-learning models 136*a-d* may include a first cardiac machine-learning model 136*a* that is configured to generate a first cardiac score 128*a* associated with a first stage of coronary heart disease 132*a*, a second cardiac machine-learning model 136*b* that is configured to generate a second cardiac score 128*b* associated with a second stage of coronary heart disease 132*b*, a third cardiac machine-learning model 136*c* that is configured to generate a third cardiac score 128*c* associated with a third stage of coronary heart disease 132*c*, a fourth cardiac machine-learning model 136*d* that is configured to generate a fourth cardiac score 128*d* associated with a fourth stage of coronary heart disease 132*d*, up to an nth cardiac machine-learning model 136*n* that is configured to generate a nth cardiac score 128*n* associated with a nth stage of coronary heart disease 132*n*, and like.

With continued reference to FIG. 1, iteratively training the set of cardiac machine learning models may include classifying the cardiac training data to one or more stages of coronary heart disease 132 of the plurality of stages of coronary heart disease 132*a-d*. This may involve the detailed classification of each data point based on its correspondence to specific stages of CHD 132*a-d*. Cardiac training data may be collected from various sources such as patient ECGs, imaging results, and biochemical markers, APIs, databases, and the like. This cardiac training data may be preprocessed and analyzed to extract relevant features that signify the presence and severity of CHD. Subsequently, the cardiac training data may be annotated with the correct stage of CHD 132*a-d*. In an embodiment, the annotation and labeling cardiac training data may be done by processor 104 or another medical professional. This may include labeling each piece of data with a stage descriptor that reflects its clinical significance in the progression of CHD. Each cardiac machine learning model 136*a-d* may be iteratively trained using the cardiac training data associated with its corresponding stage of CHD 132.

With continued reference to FIG. 1, processor 104 may use an impact score 124 to calibrate a cardiac machine learning model 136. A cardiac machine learning model 136 may be trained using epidemiological data, clinical studies, expert consensus, and the like which help to establish the relationships between various risk factors within the contextual data 120 and the various stages of CHD 132. The model may incorporate these relationships by assigning different weights or multipliers to different components of the impact score 124 based on their influence on heart disease. Assigning different weights or multipliers to the components of an impact score is used in developing a cardiac machine learning model 136. This approach allows the model to reflect the varying degrees of influence that different risk factors have on the development of CHD. Processor 104 may identify which factors should be included in the impact score 124 based on their known associations with CHD. Common factors include high blood pressure, cholesterol levels, smoking, diabetes, family history, age, and obesity. Each of these factors does not contribute equally to the risk of heart disease; their impact can vary significantly depending on their severity and the individual characteristics of the patient.

With continued reference to FIG. 1, epidemiological data may include the results from longitudinal studies, and meta-analyses to quantify how much each factor increases the risk of developing heart disease. Statistical models, such as Cox proportional hazards models or logistic regression, are often employed to estimate the relative risk associated with each factor. These statistical models may be used to generate coefficients or hazard ratios that quantify the strength of the association between each risk factor and CHD. Once the relative importance of each factor is established through these coefficients, they may be translated into weights or multipliers in the cardiac machine learning model 136. For example, smoking might be assigned a higher weight than obesity if data shows that smoking has a stronger association with CHD in the studied population. These weights are used to modify the individual scores for each risk factor in the impact score. In a non-limiting example, if a patient has a high cholesterol level, which the model identifies as a significant risk factor with a high weight, their overall impact score 124 may be increased more by this factor than by a less weighted factor, such as age, assuming all else is constant. This weighted sum approach ensures that the final cardiac score more accurately reflects the patient's personalized risk profile.

With continued reference to FIG. 1, the weighted impact scores 124 may then be integrated, often using a sum or another formulaic integration that considers not just the isolated weights but also potential interactions between risk factors. For instance, the model might include an interaction term if the combined effect of smoking and high cholesterol is greater than the sum of their individual effects.

With continued reference to FIG. 1, cardiac machine-learning models 136*a-d* may be trained to tackle the same problem of calculating multiple cardiac scores 128. In an embodiment, cardiac machine-learning models 136*a-d* may be configured to 'compete.' This may mean the outputs of these models may vie for priority. Selection of the most appropriate model or output for a particular application can be based on various criteria. For instance, the model that demonstrates the highest confidence level in its predictions might be favored. Alternatively, the model with the best overall performance metrics—such as accuracy, precision, and recall—across a validated dataset could be considered superior. In complex applications, the final decision might also integrate human oversight, where experts review and interpret the models' outputs, further refining the selection process based on nuanced criteria that go beyond quantitative measures.

With continued reference to FIG. 1, machine learning plays a crucial role in enhancing the function of software for generating a set of cardiac machine-learning models 136*a-d*. This may include identifying patterns within the ECG data 112 and contextual data 120 that lead to changes in the capabilities of the set of cardiac machine-learning models 136*a-d*. By analyzing vast amounts of data related to ECG signals, machine learning algorithms can identify patterns, correlations, and dependencies that contribute to a generating the set of cardiac machine-learning models 136*a-d*. These algorithms can extract valuable insights from various sources, including text, document, EHRs, ECG signals, and the like. By applying machine learning techniques, the software can generate the set of cardiac machine-learning models 136*a-d* extremely accurately. Machine learning models may enable the software to learn from past collaborative experiences of the entities and iteratively improve its training data over time.

With continued reference to FIG. 1, processor 104 may be configured to update the cardiac training data of the set of cardiac machine-learning models 136*a-d* using user inputs. A set of cardiac machine-learning models 136*a-d* may use user input to update its training data, thereby improving its performance, speed, and accuracy. In embodiments, the set of cardiac machine-learning models 136*a-d* may be iteratively updated using input and output results of past iterations of the set of cardiac machine-learning models 136*a-d*. The set of cardiac machine-learning models 136*a-d* may then be iteratively retrained using the updated cardiac training data. For instance, and without limitation, set of cardiac machine-learning models 136*a-d* may be trained using a first training data from, for example, and without limitation, training data from a user input or database. The set of cardiac machine-learning models 136*a-d* may then be updated by using previous inputs and outputs from the set of cardiac machine-learning models 136*a-d* as second set of training data to then retrain the cardiac machine learning models. This process of updating the set of cardiac machine-learning models 136*a-d* and their associated training data may be continuously done to create subsequent cardiac machine-learning models 136 to improve the speed and accuracy of the set of cardiac machine-learning models 136*a-d*. When users interact with the software, their actions, preferences, and feedback provide valuable information that can be used to refine and enhance the model. This user input is collected and incorporated into the training data, allowing the machine learning model to learn from real-world interactions and adapt its predictions accordingly. By continually incorporating user input, the model becomes more responsive to user needs and preferences, capturing evolving trends and patterns. This iterative process of updating the training data with user input enables the machine learning model to deliver more personalized and relevant results, ultimately enhancing the overall user experience. The discussion within this paragraph may apply to both the cardiac machine-learning models 136*a-d* or any other machine-learning model/classifier discussed herein.

Incorporating the user feedback may include updating the training data by removing or adding correlations of subject data to a path or resources as indicated by the feedback. Any machine-learning model as described herein may have the training data updated based on such feedback or data gathered using a web crawler as described above. For example, correlations in training data may be based on outdated information wherein, a web crawler may update such correlations based on more recent resources and information.

With continued reference to FIG. 1, processor 104 may use user feedback to train the machine-learning models and/or classifiers described above. For example, machine-learning models and/or classifiers may be trained using past inputs and outputs of the machine-learning model. In some embodiments, if user feedback indicates that an output of machine-learning models and/or classifiers was "bad," then that output and the corresponding input may be removed from training data used to train machine-learning models and/or classifiers, and/or may be replaced with a value entered by, e.g., another value that represents an ideal output given the input the machine learning model originally received, permitting use in retraining, and adding to training data; in either case, machine-learning models may be retrained with modified training data as described in further detail below. In some embodiments, training data of classifier may include user feedback.

With continued reference to FIG. 1, in some embodiments, an accuracy score may be calculated for the machine-learning model and/or classifier using user feedback. For the purposes of this disclosure, "accuracy score," is a numerical value concerning the accuracy of a machine-learning model. For example, the accuracy/quality of the output set of cardiac machine-learning models 136*a-d* may be averaged to determine an accuracy score. In some embodiments, an accuracy score may be determined for pairing of entities. Accuracy score or another score as described above may indicate a degree of retraining needed for a machine-learning model and/or classifier. Processor 104 may perform a larger number of retraining cycles for a higher number (or lower number, depending on a numerical interpretation used), and/or may collect more training data for such retraining. The discussion within this paragraph and the paragraphs preceding this paragraph may apply to both the set of cardiac machine-learning models 136*a-d* or any other machine-learning model/classifier mentioned herein.

With continued reference to FIG. 1, each cardiac score 128 of the set of cardiac scores 128*a-d* may include a confidence interval 140. The confidence interval 140 may be used to reflect the likelihood that the patient's condition falls within a given stage of CHD 132. As used in the current disclosure, a "confidence interval" is a statistical concept used to express the degree of uncertainty associated with a sample statistic. A confidence interval 140 may delineate a range of values that is statistically expected to encompass the actual value of a population parameter—like a mean or proportion—related to cardiac health, with a specified level of certainty. The confidence interval 140 associated with each cardiac score 128*a-d* serves to quantify the degree of certainty with which a patient's condition can be categorized into a specific stage of CHD 132*a-d*. For instance, a cardiac score for stage 132*a* (no apparent plaque) might come with a confidence interval 140 that suggests a 95% probability that the true state of the patient's coronary health indeed falls within the parameters defined for this stage-namely, a TPV of 0 and a PAV of 0%. This interval is derived from sample data and indicates the estimated range which, upon multiple iterations of the same measurement or study, is predicted to contain the true population parameter a specified percentage of the time. For example, a 95% confidence interval 140 around a cardiac score means that in 95 out of 100 similar studies, this interval would include the actual population parameter. This statistical tool adds a layer of understanding to the cardiac scores by highlighting the reliability of the estimates and helping clinicians gauge the precision of the measurements involved in cardiac health assessments.

With continued reference to FIG. 1, processor 104 is configured to select at least one stage of coronary heart disease 144 of a plurality of stages of coronary heart disease 132*a-d* of the subject as a function of the set of cardiac scores 128*a-d*. As used in the current disclosure, a "selected stage of CHD" is a stage of CHD that is associated with the subject's current condition. Selecting the stage of CHD 144 using a processor may involve algorithms and data analysis techniques. The processor may receive and compile cardiac scores 128*a-d*, each derived from different cardiac machine-learning models 136*a-d* trained on data characteristic of various CHD stages. Each cardiac score 128 within the set may be specifically associated with a distinct stage of CHD, reflecting varying levels of disease severity from initial to advanced stages. Each score from the set of cardiac scores 128*a-d* may be pre-associated with a specific stage of CHD 132*a-d*. The decision-making algorithm implemented by the processor 104 may begin by comparing these scores against established clinical thresholds. These clinical threshold may be validated through research and clinical trials. The processor may then analyze these scores to determine which score or combination of scores most accurately reflects the patient's condition. In an embodiment, processor 104 may select a stage of CHD 144 by evaluating the confidence interval 140 of each cardiac score 128*a-d*. The processor 104 may evaluate the confidence intervals 140 of the scores to assess their reliability. A narrower confidence interval indicates higher precision of the cardiac score, whereas a wider interval suggests greater uncertainty. The processor 104 may consider not only the score itself but also the width of its confidence interval to determine which stage of CHD is most likely represented by the data. To select the appropriate CHD stage 144, processor 104 may apply a set of decision rules that incorporate both the cardiac scores and their confidence intervals. For instance, if a particular cardiac score significantly exceeds the threshold for a specific stage and has a narrow confidence interval, the processor might lean towards selecting that stage. Conversely, if the highest cardiac score has a wide confidence interval, the processor might look for additional evidence in the scores for other stages or use aggregate data from multiple scores to make a more informed decision. In an embodiment, processor 104 may select the stage of CHD 144 with the most favorable confidence interval 140. This may include selecting the score that surpasses a confidence threshold. However, the processor may also employ a more complex decision-making logic, such as integrating multiple scores to evaluate their collective impact-especially in borderline cases where single-score assessments may not provide a clear picture. Once a potential CHD stage is selected based on the scores, the processor may further refine its decision by integrating additional patient data such as previous medical history, current symptoms, and other relevant health indicators. This holistic approach ensures that the selected CHD stage is not only based on quantitative scores but is also corroborated by qualitative clinical insights.

With continued reference to FIG. 1, processor 104 may leverage the use of fuzzy inferencing systems and/or machine learning to synthesize a cardiac score. Leveraging both fuzzy inferencing and machine learning (ML) can significantly enhance the synthesis and interpretation of cardiac scores. For instance, the processor 104 might employ a combination of multiple machine learning models to aggregate and refine these cardiac scores 128. This approach allows the integration of different diagnostic dimensions, such as the severity of ECG abnormalities and various risk factors, to generate a comprehensive cardiac scores 128. By utilizing techniques like fuzzy logic, the processor can handle imprecise inputs and integrate them to produce a more nuanced assessment of heart disease stages. In scenarios where the outputs of two or more ML models are considered, the combination could be optimized either by selecting the output with the highest confidence level or by synthesizing outputs using a weighted average or other mathematical models that consider the performance metrics of each contributing model. This method ensures a more accurate and reliable cardiac score that aids clinicians in making informed decisions regarding patient care and treatment strategies.

With continued reference to FIG. 1, processor 104 may be configured to generate a treatment plan 148 as a function of the selected stage of CHD 144. As used in the current disclosure, a "treatment plan" is an outline developed to manage a patient's specific health condition. A treatment plan may detail the therapeutic strategies, interventions, and actions to be taken to address the patient's medical needs. A treatment plan may be based on a thorough diagnosis and tailored to the individual's subject profile 108. Once the selected stage of CHD 144 has been identified, processor 104 may outline a treatment plan tailored to the specific needs and condition of the patient. This plan may include various components such as medication, lifestyle changes, possible interventions, and monitoring strategies, all adapted to the severity and specifics of the CHD stage 148. Once the stage of CHD is accurately determined, processor 104 may leverage a database of treatment protocols aligned with each stage of CHD 132*a-d*, refined through clinical research and practice guidelines. The processor 104 may then match the selected CHD stage 144 with corresponding treatment strategies, considering the nuances reflected in the contextual data 120. This could involve recommendations for medical interventions, surgical options, lifestyle adjustments, and necessary follow-up care tailored to the patient's specific needs. In an embodiment, processor 104 may apply machine learning algorithms and decision-making logic to dynamically generate a treatment plan 148 that not only addresses the immediate health issues associated with the current stage of CHD 144 but also anticipates potential complications and integrates preventive strategies to improve long-term outcomes. This ensures that each treatment plan 148 is not only comprehensive but also personalized, enhancing its effectiveness and adaptability to patient-specific conditions and responses to treatment.

With continued reference to FIG. 1, after accurately selecting the stage of CHD 144, processor 104 may proceed to select suitable treatment plans 148. In a non-limiting example, in early stages like a first stage of CHD 132*a*, the processor might recommend preventive strategies focused on lifestyle modifications such as diet adjustments, increased physical activity, and smoking cessation, possibly supplemented by preventive medications like aspirin or statins based on the risk profile. As the severity of the disease progresses to second stage of CHD 132*b*, the treatment plan 148 may introduce medications to manage symptoms and prevent further progression, alongside continuing emphasis on lifestyle changes. In these stages, regular monitoring through non-invasive tests might also be recommended to track disease progression. For more advanced stages, such as the fourth stage of CHD 132*d*, the treatment plan 148 may become significantly more intensive. Processor 104 may suggest more aggressive interventions including angioplasty, coronary artery bypass grafting, or even heart transplants, depending on the severity of the blockage and damage. These stages may also necessitate the integration of cardiac rehabilitation programs and management of complications like heart failure.

With continued reference to FIG. 1, processor 104 may generate treatment plan 148 using a treatment machine-learning model 152. As used in the current disclosure, a "treatment machine-learning model" is a machine-learning model that is configured to generate treatment plan 148. Treatment machine-learning model 152 may be consistent with the machine-learning model described below in FIG. 2. Inputs to the treatment machine-learning model 152 may include contextual data 120, subject profile 108, EHR 116, impact score 124, ECG data 112, severity scores, examples of treatment plan 148, and the like. Outputs to the treatment machine-learning model 152 may include treatment plan 148 tailored to the contextual data 120 and selected stage of CHD 144. Treatment training data may include a plurality of data entries containing a plurality of inputs that are correlated to a plurality of outputs for training a processor by a machine-learning process. In an embodiment, treatment training data may include a plurality of contextual data 120 and selected stage of CHD 144 correlated to examples of treatment plan 148. Treatment training data may be received from database 300. Treatment training data may contain information about contextual data 120, subject profile 108, EHR 116, impact score 124, ECG data 112, severity scores, examples of treatment plan 148, and the like. In an embodiment, treatment training data may be iteratively updated as a function of the input and output results of past treatment machine-learning model 152 or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

Still referring to FIG. 1, processor 104 may be configured to display the treatment plan 148 or the selected stage of CHD 144 using a display device 156. As used in the current disclosure, a "display device" is a device that is used to display a plurality of data and other digital content. A display device 156 may include a user interface. A "user interface," as used herein, is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pulldown menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

With continued reference to FIG. 1, methods of evaluating the stages of coronary heart disease may be consistent with the methods disclosed in Non-provisional application Ser. No. 18/229,854, filed on Aug. 3, 2023 and entitled "APPARATUS AND METHOD FOR DETERMINING A PATIENT SURVIVAL PROFILE USING ARTIFICIAL INTELLIGENCE-ENABLED ELECTROCARDIOGRAM (ECG)," Patent Cooperation Treaty (PCT) Application No. PCT/US2023/022325, filed on May 16, 2023, and entitled "DEEP LEARNING ENABLED ELECTROCARDIOGRAPHIC PREDICTION OF COMPUTER TOMOGRAPHY-BASED HIGH CORONARY CALCIUM SCORE (CAC)," U.S. Non-provisional application Ser. No. 18/642,012, filed on Apr. 22, 2024, and entitled "SYSTEM AND A METHOD FOR ELECTROCARDIOGRAPHIC PREDICTION OF COMPUTED TOMOGRAPHY-BASED HIGH CORONARY CALCIUM SCORE," both of which are incorporated herein by reference. As a non-limiting example, one or more of set of cardiac machine-learning models 136 may include a model configured to generate a coronary calcium score consistent with the disclosure of applications PCT/US2023/022325 and Ser. No. 18/642,012, above. As a non-limiting example, one or more of set of cardiac machine-learning models 136 may include a model configured to generate a condition score consistent with the disclosure of application Ser. No. 18/229,854.

Figure 2:
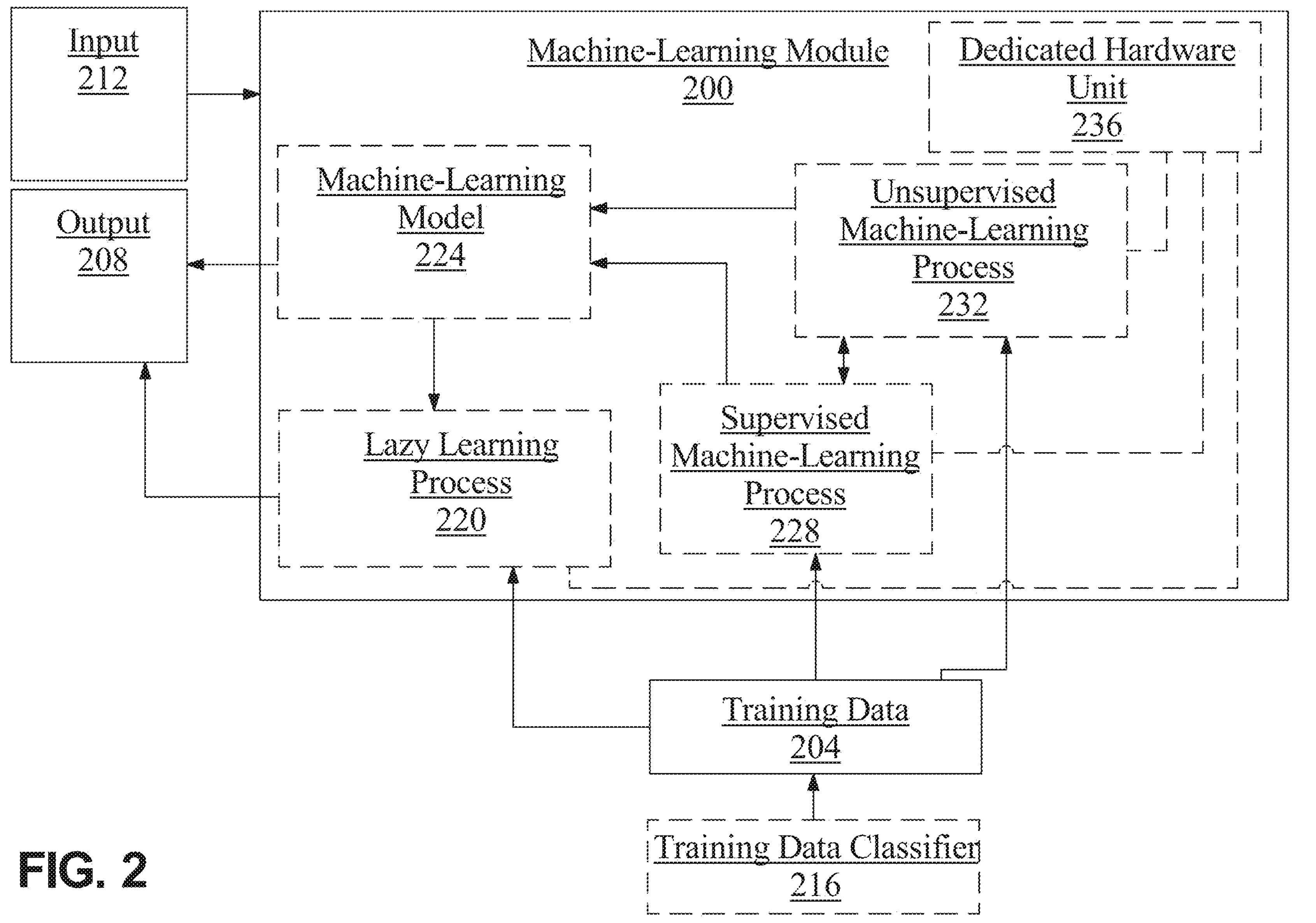
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example examples of ECG data and examples of contextual data as inputs correlated to examples of cardiac scores as outputs.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to classify cardiac training data to one or more stages of CHD 132*a-d*.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, subject data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include examples of ECG data and examples of contextual data as described above as inputs, examples of cardiac scores as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods.

Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
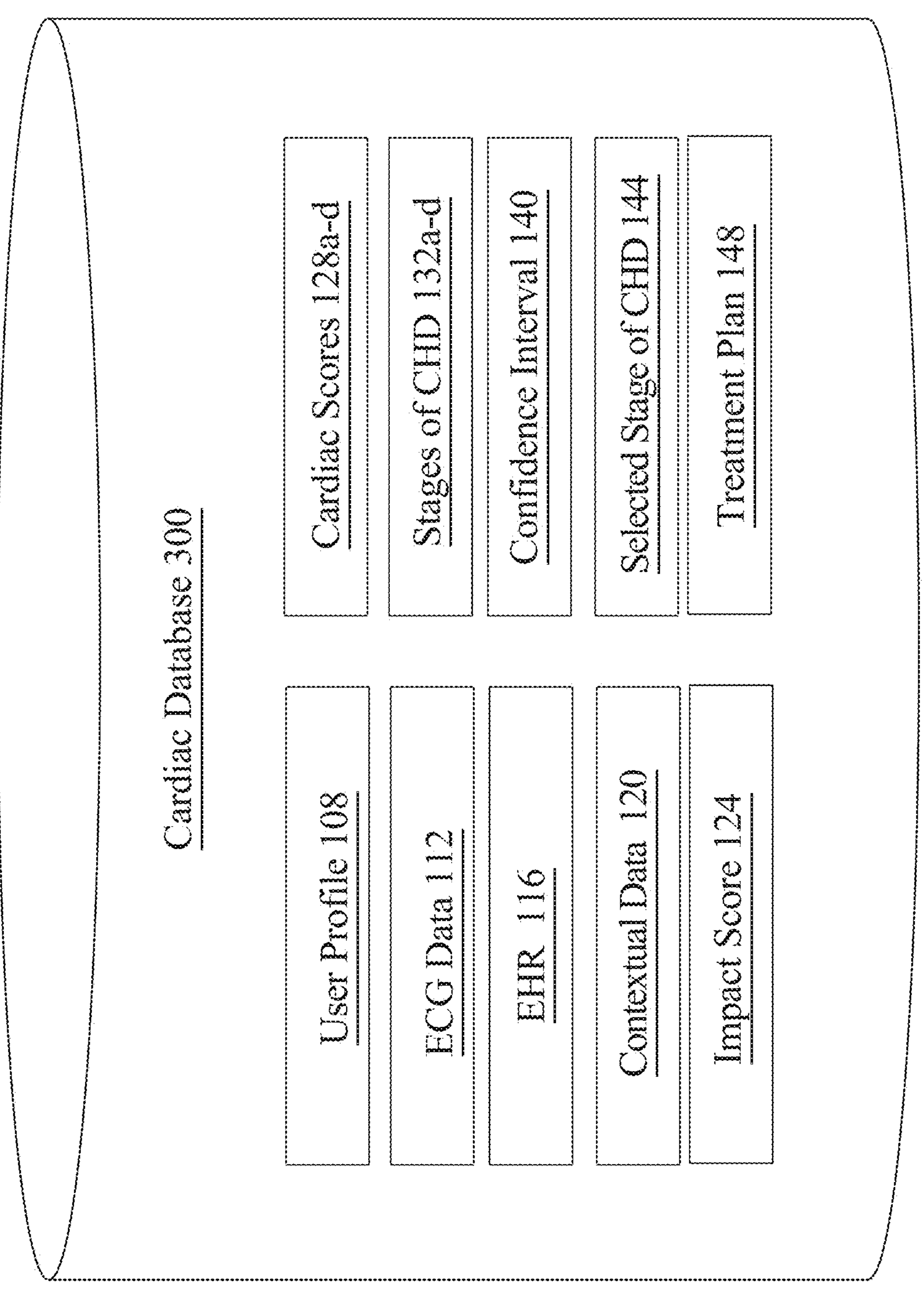
FIG. 3 is a block diagram of an exemplary embodiment of a cardiac database.

Now referring to FIG. 3, an exemplary cardiac database 300 is illustrated by way of block diagram. In an embodiment, any past or present versions of any data disclosed herein may be stored within the cardiac database 300 including but not limited to: contextual data 120, subject profile 108, EHR 116, impact score 124, ECG data 112, treatment plan 148, selected stage of CHD 144, and the like. Processor 104 may be communicatively connected with cardiac database 300. For example, in some cases, database 300 may be local to processor 104. Alternatively or additionally, in some cases, database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network. cardiac database 300 may be implemented, without limitation, as a relational database, a key-value retrieval database such as a NOSQL database, or any other format or structure for use as a database that a person skilled in the art would recognize as suitable upon review of the entirety of this disclosure. cardiac database 300 may alternatively or additionally be implemented using a distributed data storage protocol and/or data structure, such as a distributed hash table or the like. Cardiac database 300 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 4:
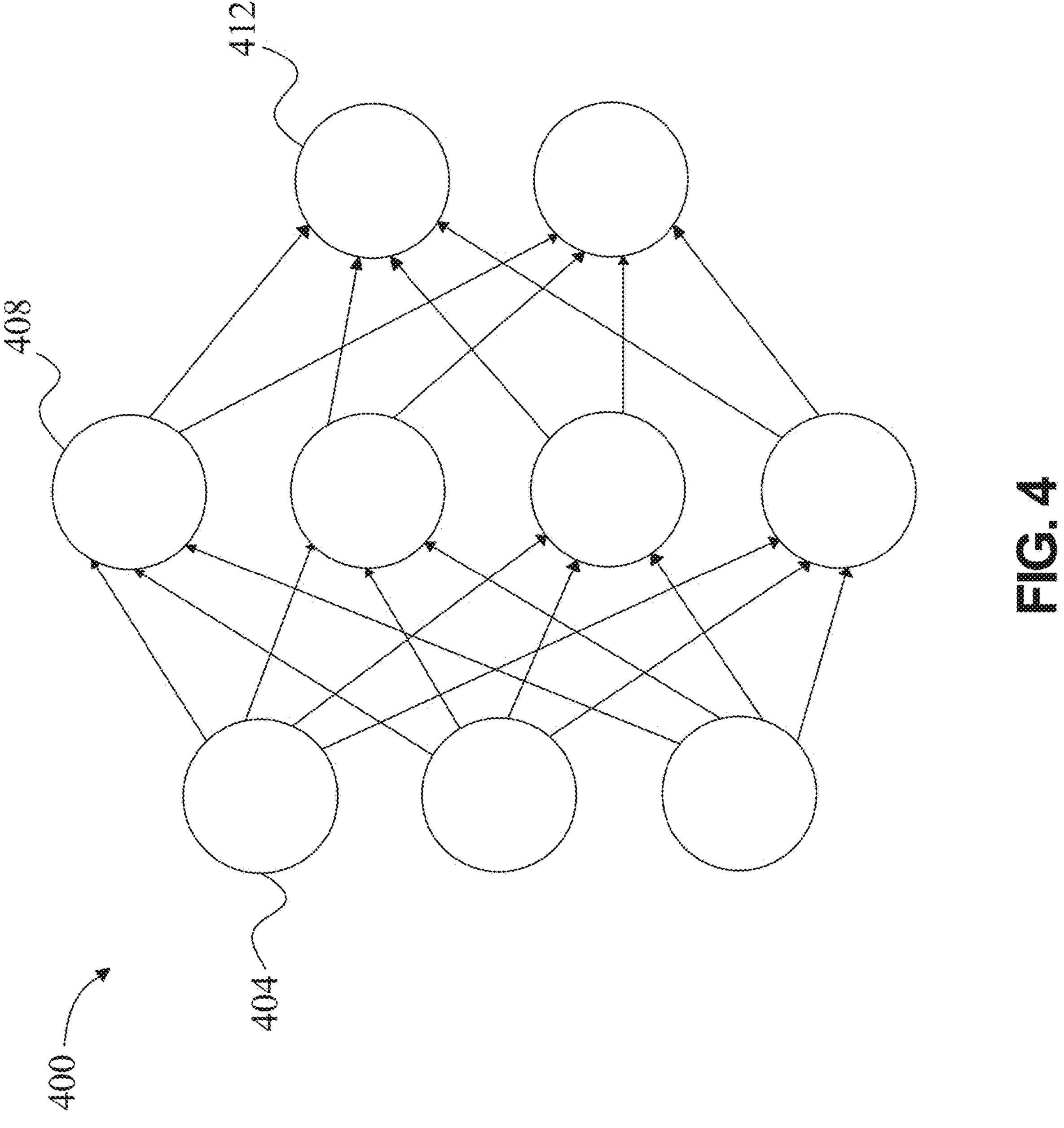
FIG. 4 is a diagram of an exemplary embodiment of a neural network.

Referring now to FIG. 4, an exemplary embodiment of neural network 400 is illustrated. A neural network 400, also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
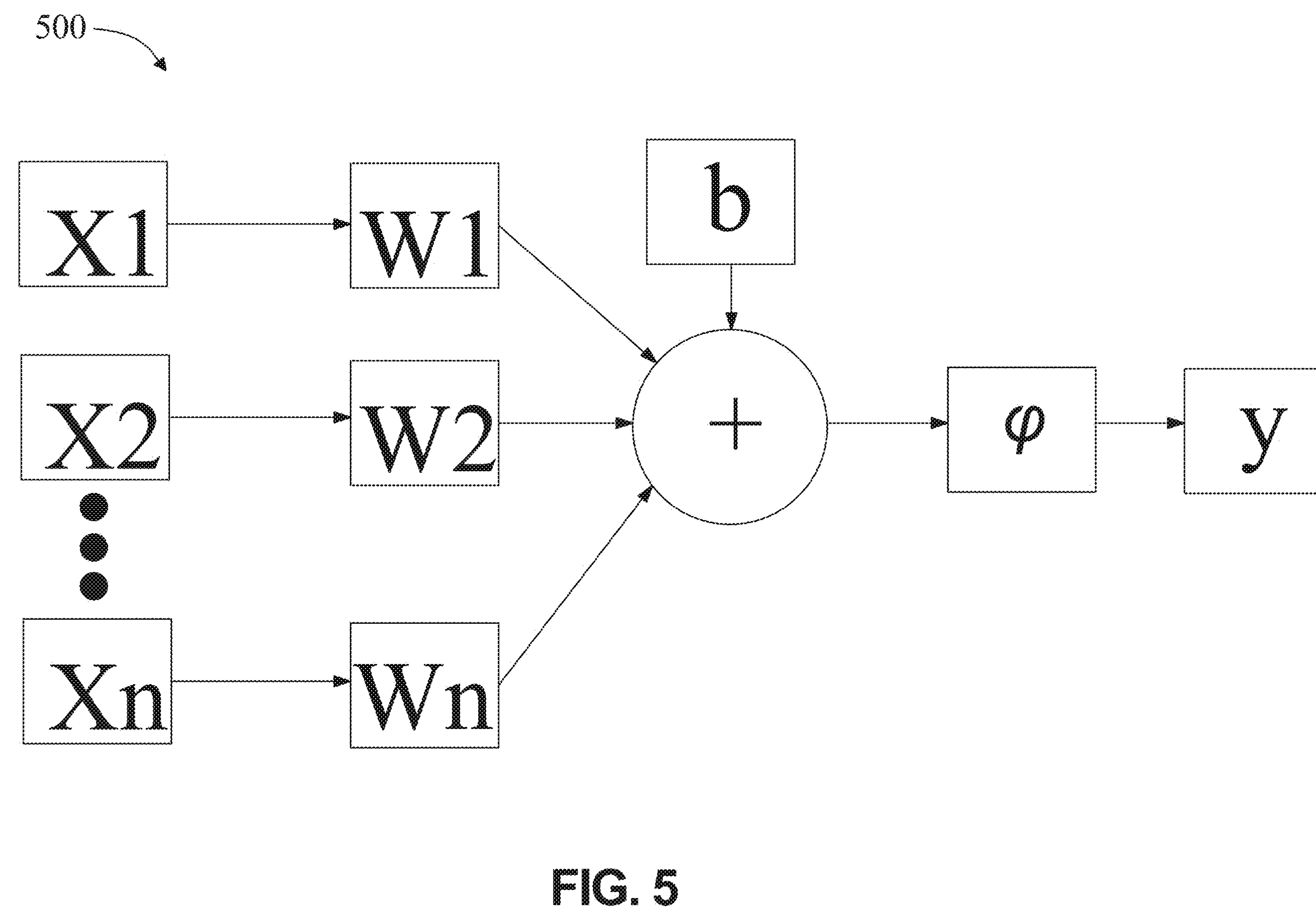
FIG. 5 is a diagram of an exemplary embodiment of a node of a neural network.

Referring now to FIG. 5, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
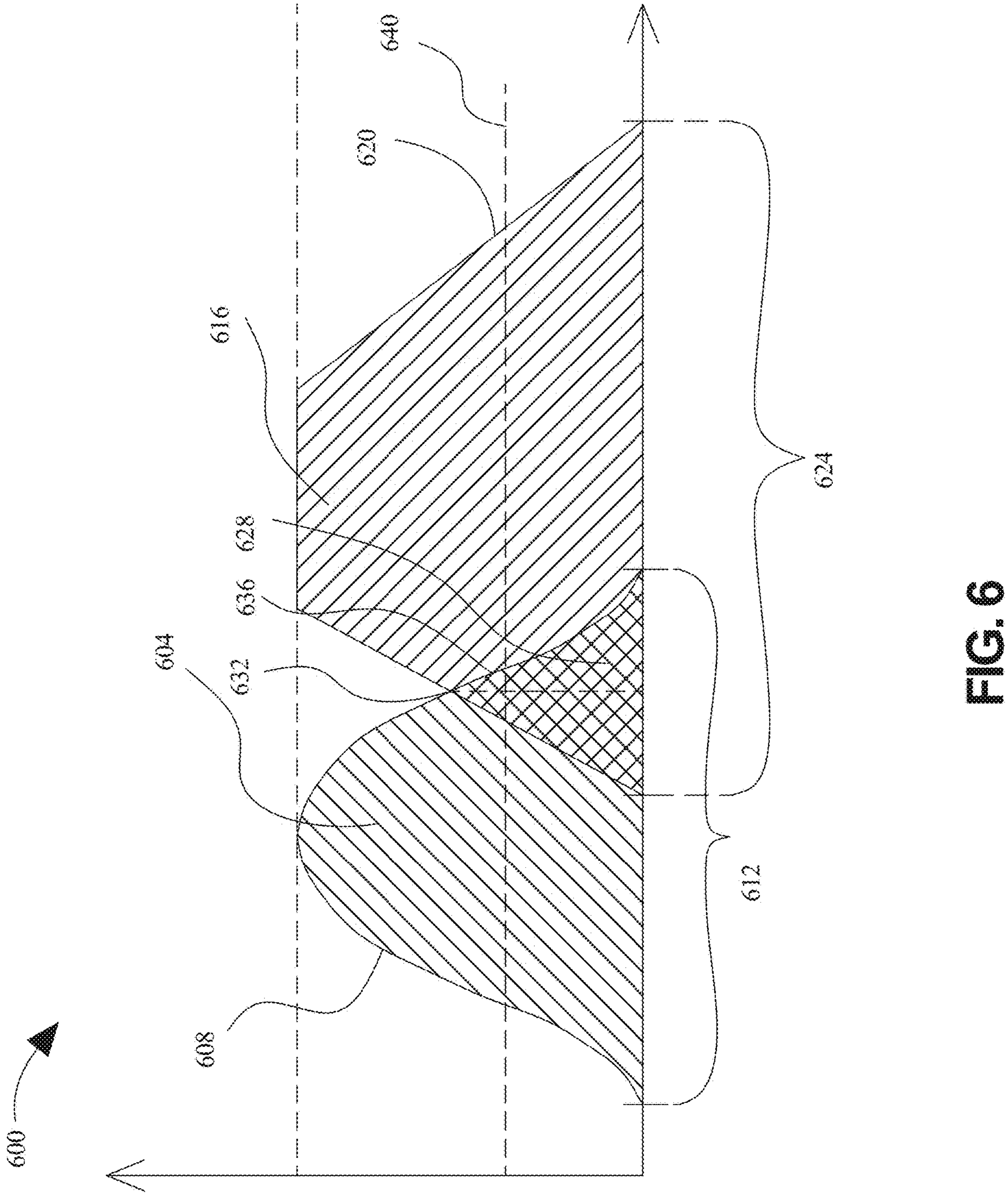
FIG. 6 is an illustration of an exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting the fuzzy set comparison 600 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent ECG data 112 and examples of cardiac scores from FIG. 1.

Alternatively or additionally, and still referring to FIG. 6, fuzzy set comparison 600 may be generated as a function of determining the data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input ECG data 112 and examples of cardiac scores. For instance, an acceptance variable may represent a first measurable value pertaining to the classification of ECG data 112 to examples of cardiac scores. Continuing the example, an output variable may represent cardiac scores 128 associated with the subject. In an embodiment, ECG data 112 and/or examples of cardiac scores may be represented by their own fuzzy set. In other embodiments, the classification of the data into Cardiac scores 128 may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T (T(a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$(x, a, b, c) = \begin{cases} 0, & \text{for } x > c \text{ and } x < a \\ \frac{x-a}{b-a}, & \text{for } a \le x < b \\ \frac{c-x}{c-b}, & \text{if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any ECG data 112 and examples of cardiac scores. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, the classification into one or more query categories may indicate a sufficient degree of overlap with fuzzy set representing ECG data 112 and examples of cardiac scores for combination to occur as described above. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if both ECG data 112 and examples of cardiac scores have fuzzy sets, Cardiac scores 128 may be generated by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7:
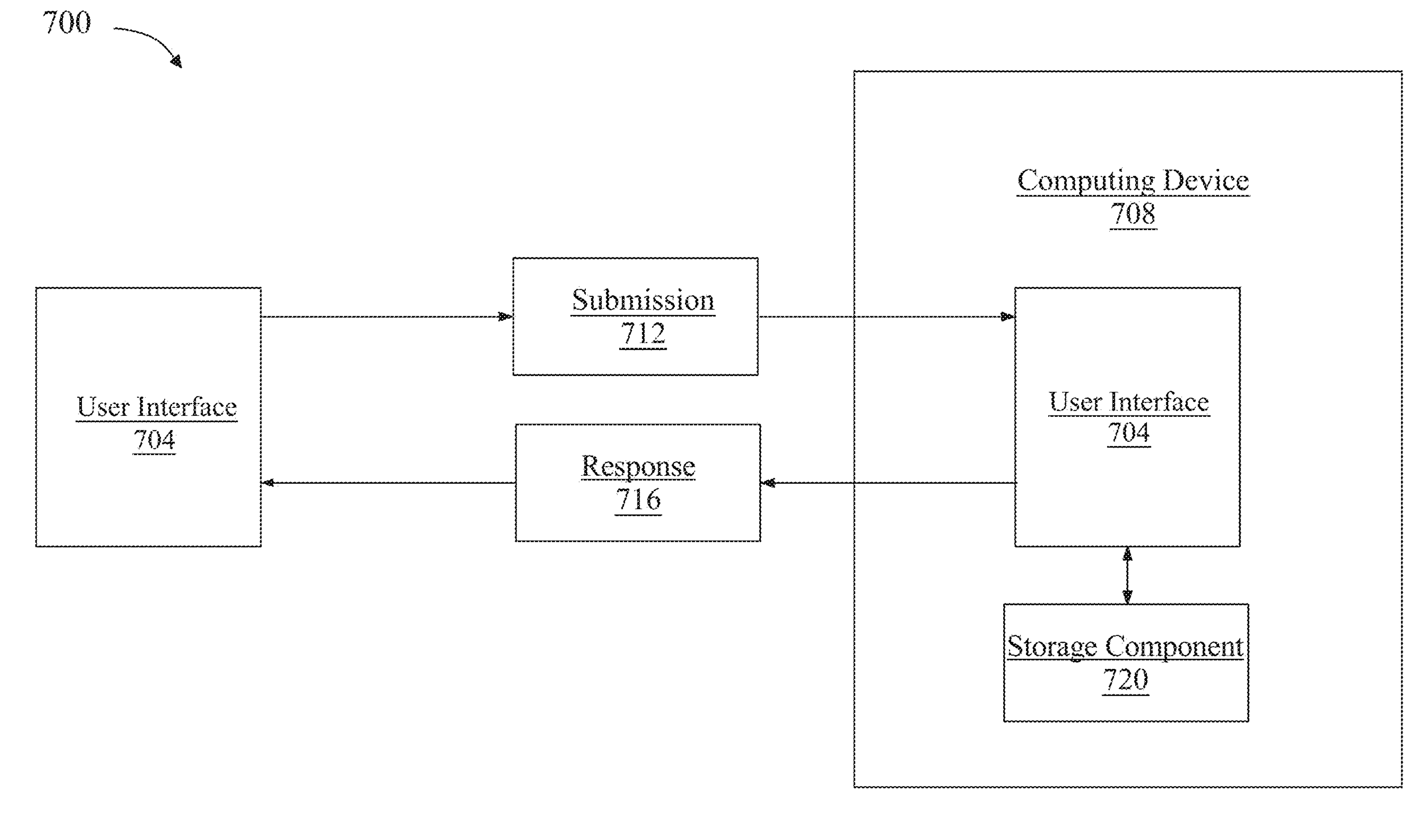
FIG. 7 is an illustration of an exemplary embodiment of a chatbot.

Referring to FIG. 7, a chatbot system 700 is schematically illustrated. According to some embodiments, a user interface 704 may be communicative with a computing device 708 that is configured to operate a chatbot. In some cases, user interface 704 may be local to computing device 708. Alternatively or additionally, in some cases, user interface 704 may remote to computing device 708 and communicative with the computing device 708, by way of one or more networks, such as without limitation the internet. Alternatively or additionally, user interface 704 may communicate with user device 708 using telephonic devices and networks, such as without limitation fax machines, short message service (SMS), or multimedia message service (MMS). Commonly, user interface 704 communicates with computing device 708 using text-based communication, for example without limitation using a character encoding protocol, such as American Standard for Information Interchange (ASCII). Typically, a user interface 704 conversationally interfaces a chatbot, by way of at least a submission 712, from the user interface 708 to the chatbot, and a response 716, from the chatbot to the user interface 704. In many cases, one or both submission 712 and response 716 are text-based communication. Alternatively or additionally, in some cases, one or both of submission 712 and response 716 are audio-based communication.

Continuing in reference to FIG. 7, a submission 712 once received by computing device 708 operating a chatbot, may be processed by a processor. In some embodiments, processor processes a submission 712 using one or more keyword recognition, pattern matching, and natural language processing. In some embodiments, processor employs real-time learning with evolutionary algorithms. In some cases, processor may retrieve a pre-prepared response from at least a storage component 720, based upon submission 712. Alternatively or additionally, in some embodiments, processor communicates a response 716 without first receiving a submission 712, thereby initiating conversation. In some cases, processor communicates an inquiry to user interface 704; and the processor is configured to process an answer to the inquiry in a following submission 712 from the user interface 704. In some cases, an answer to an inquiry present within a submission 712 from a user device 704 may be used by computing device 708 as an input to another function.

With continued reference to FIG. 7, A chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "Chatbot input" is any response that a candidate or employer inputs in to a chatbot as a response to a prompt or question.

With continuing reference to FIG. 7, computing device 708 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 708 may generate two or more decision trees, which may overlap; for instance, a root node of one tree may connect to and/or receive output from one or more terminal nodes of another tree, intermediate nodes of one tree may be shared with another tree, or the like.

Still referring to FIG. 7, computing device 708 may build decision tree by following relational identification; for example, relational indication may specify that a first rule module receives an input from at least a second rule module and generates an output to at least a third rule module, and so forth, which may indicate to computing device 708 an in which such rule modules will be placed in decision tree.

Building decision tree may include recursively performing mapping of execution results output by one tree and/or subtree to root nodes of another tree and/or subtree, for instance by using such execution results as execution parameters of a subtree. In this manner, computing device 708 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 7, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Referring now to FIG. 8, an illustration of an exemplary cardiac report. Processor 104 may be configured to generate a cardiac report 800 as a function of the selected stage of coronary heart disease. As used in the current disclosure, a "cardiac report" is summary of the patient's cardiovascular health. A cardiac report 800 may provide a detailed and comprehensive, integrating diagnostic data, stage classification, and tailored treatment recommendations. This report typically begins with an overview of the patient's diagnostic results, including the identification of the specific stage of CHD 148. Report 800 may include details regarding the identified stage, explaining the characteristics and implications of this stage within the context of the patient's overall health. The report may outline recommended treatment plans that align with the current stage, ranging from lifestyle modifications and medications to potential surgical interventions if needed. Additionally, the report may include follow-up strategies and monitoring schedules to ensure ongoing evaluation of the patient's condition.

With continued reference to FIG. 8, processor 104 may generate a cardiac report 800 by following structuring the selected stage of CHD along with the treatment plan. This report not only outlines the diagnostic findings and the CHD stage but also details the recommended interventions and follow-up schedule. It might also include prognostic information, helping clinicians and patients understand the expected outcomes and timelines for improvement or progression of the disease. The completed report is then made available to healthcare providers for review and further action, ensuring that all information is presented clearly and concisely to facilitate informed decision-making and optimize patient care. The cardiac report 800 may be generated using a machine learning model as described herein above.

Figure 9:
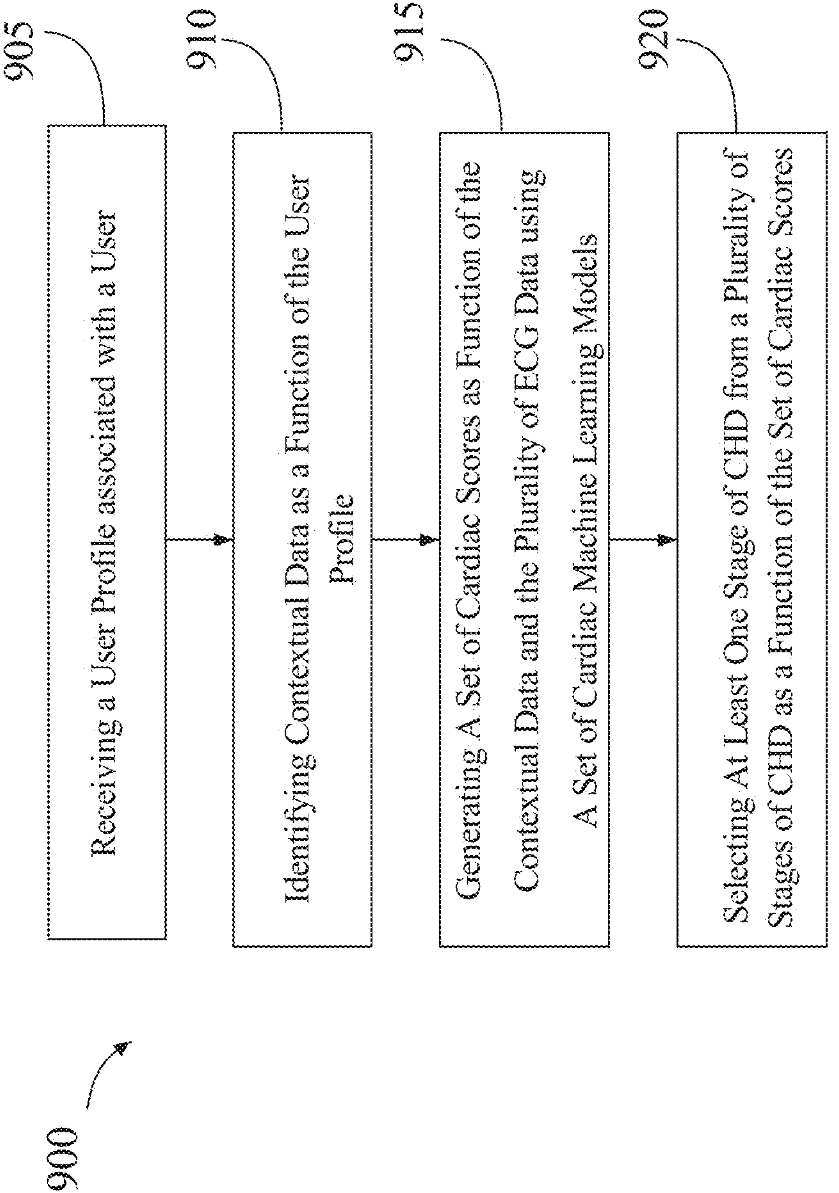
FIG. 9 is a flow diagram of an exemplary method for identifying the progression of coronary heart disease.

Referring now to FIG. 9, a flow diagram of an exemplary method 900 for identifying the progression of coronary heart disease is illustrated. At step 905, method 900 includes receiving, using the at least a processor, a subject profile associated with a subject, wherein the subject profile comprises a plurality of electrocardiogram (ECG) data. This may be implemented as described and with reference to FIGS. 1-9. In some cases, receiving the subject profile may include receiving the subject profile from an electronic medical record.

Still referring to FIG. 9, at step 910, method 900 includes identifying, using the at least a processor, contextual data as a function of the subject profile. This may be implemented as described and with reference to FIGS. 1-9. In an embodiment, the method may include generating, using the at least a processor, an impact score as a function of the contextual data. In some cases, iteratively training the set of cardiac machine learning models may additionally include calibrating each cardiac machine learning model of the set of cardiac machine learning models using the impact score.

Still referring to FIG. 9, at step 915, method 900 includes generating, using the at least a processor, a set of cardiac scores as function of the contextual data and the plurality of ECG data using a set of cardiac machine learning models. Generating the set of cardiac scores includes iteratively training the set of cardiac machine learning models using cardiac training data, wherein the cardiac training data comprises examples of ECG data and examples of contextual data as inputs correlated to examples of cardiac scores as outputs. Generating the set of cardiac also includes generating the set of cardiac scores using the trained set of cardiac machine learning models. This may be implemented as described and with reference to FIGS. 1-9. In an embodiment, the set of cardiac scores may include at least one cardiac score associated with each stage of coronary heart disease of the plurality of stages of coronary heart disease. Also, the set of cardiac machine learning models may include at least one cardiac machine learning model associated with each stage of coronary heart disease of the plurality of stages of coronary heart disease. In some cases, iteratively training the set of cardiac machine learning models may include classifying the cardiac training data to one or more stages of coronary heart disease of the plurality of stages of coronary heart disease and iteratively training each cardiac machine learning model of the set of cardiac machine learning models using the cardiac training data associated with the one or more stages of coronary heart disease. In some cases, each cardiac score of the set of cardiac scores comprises a confidence interval.

Still referring to FIG. 9, at step 920, method 900 includes selecting, using the at least a processor, at least one stage of coronary heart disease from a plurality of stages of coronary heart disease as a function of the set of cardiac scores. This may be implemented as described and with reference to FIGS. 1-9. In an embodiment, the method further may include identifying, using the at least a processor, a treatment plan as a function of identification of the at least one stage of coronary heart disease of the subject. In an additional embodiment, the plurality of stages of coronary heart disease may include a plurality of ranges of total plaque volume (TPV) and/or percent arterial volume (PAV) associated with the subject.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
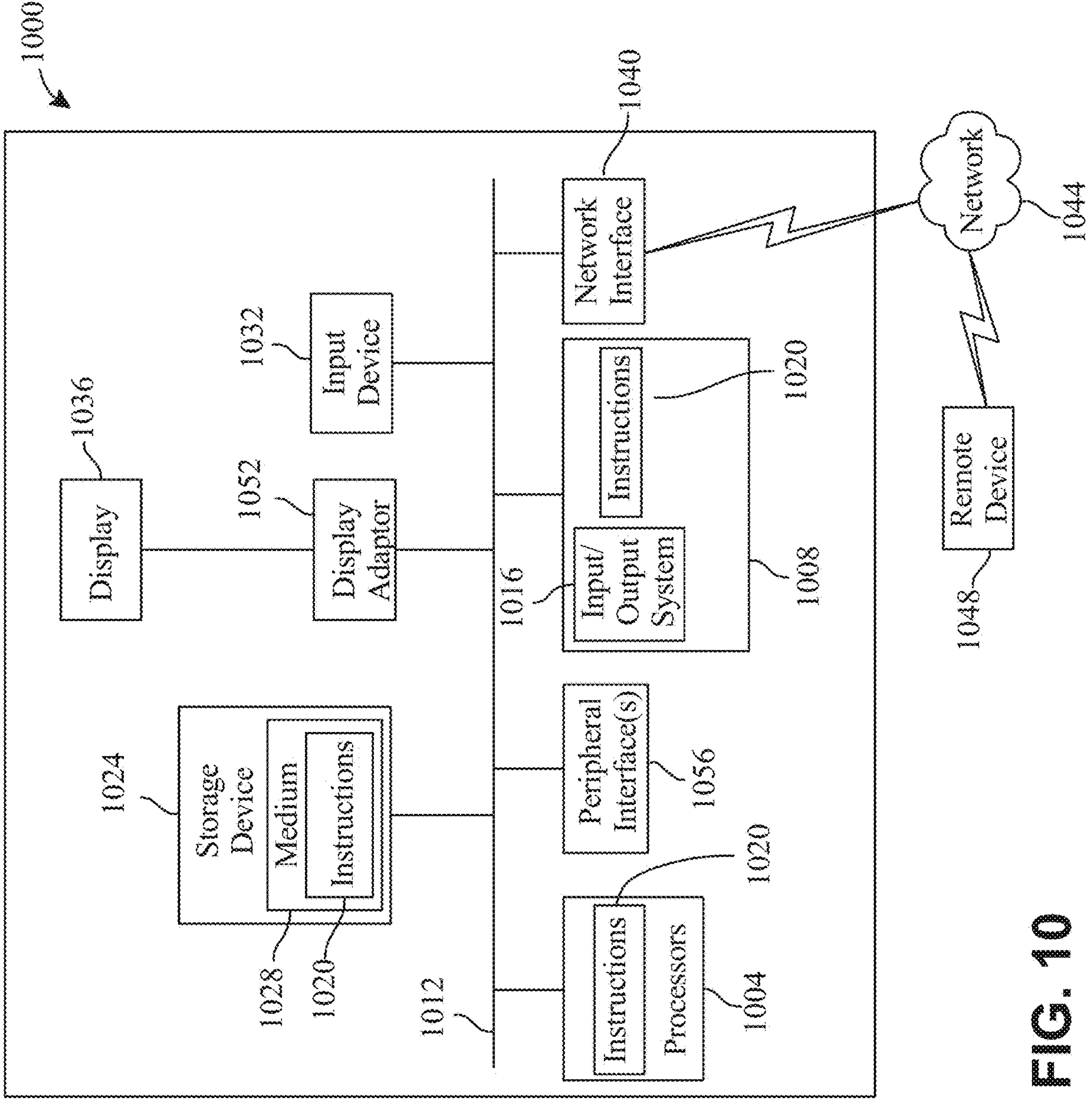
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for identifying a progression of coronary heart disease, wherein the apparatus comprises:
   - at least one processor; and
   - a memory communicatively connected to the at least one processor, wherein the memory contains instructions configuring the at least one processor to:
     - receive a subject profile associated with a subject from an electronic health record (EHR) comprising a plurality of multi-modal data associated with the subject, wherein the subject profile comprises a plurality of electrocardiogram (ECG) data, and wherein receiving the subject profile further comprises:
       - utilizing optical character recognition (OCR) to convert the EHR into machine-encoded text by pre-processing using a de-skew process at least an image of a written text; and
       - extracting features from the EHR to reduce a dimensionality of a representation of the EHR;
     - identify contextual data as a function of the subject profile;
     - generate a set of cardiac scores as a function of the contextual data and the plurality of ECG data, wherein each cardiac score of the set of cardiac scores comprises a confidence interval indicating an accuracy of each cardiac score, and wherein generating the set of cardiac scores comprises;
       - training a set of cardiac machine learning models, wherein:
         - each cardiac machine learning model of the set of cardiac machine learning models is associated with at least one stage of a plurality of stages of a coronary heart disease; and
         - each cardiac machine learning model of the set of cardiac machine learning models is trained using cardiac training data associated with its corresponding stage of coronary heart disease; and generating at least one cardiac score of the set of cardiac scores for each cardiac machine learning model of the set of cardiac machine learning models;

select one or more stages of the coronary heart disease from a plurality of stages of the coronary heart disease as a function of the set of cardiac scores and the set of confidence intervals; and display a predicted diagnosis associated with the subject and through a user interface, wherein the predicted diagnosis comprises the one or more stages of the coronary heart disease.

2. The apparatus of claim 1, wherein generating the set of cardiac scores comprises:

iteratively training the set of cardiac machine learning models using cardiac training data, wherein the cardiac training data comprises a plurality of exemplary ECG data and a plurality of exemplary contextual data as inputs correlated to a plurality of exemplary of cardiac scores as outputs, and wherein iteratively training the set of cardiac machine learning models comprises:

classifying the cardiac training data into a plurality of cardiac training subsets associated with the plurality of stages of coronary heart disease;

iteratively training each cardiac machine learning model of the set of cardiac machine learning models using each cardiac training subset of the plurality of cardiac training subsets; and generating the set of cardiac scores using the trained set of cardiac machine learning models.

3. The apparatus of claim 1, wherein the plurality of stages of the coronary heart disease comprises a plurality of ranges of total plaque volume (TPV) associated with the subject.

4. The apparatus of claim 1, wherein the memory further instructs the at least one processor to generate an impact score as a function of the contextual data.

5. The apparatus of claim 4, wherein iteratively training the set of cardiac machine learning models additionally comprises calibrating each cardiac machine learning model of the set of cardiac machine learning models using the impact score.

6. The apparatus of claim 1, wherein receiving the subject profile comprises receiving the subject profile from an electronic medical record.

7. A method for identifying a progression of coronary heart disease, wherein the method comprises:

receiving, using at least one processor, a subject profile associated with a subject from an electronic health record (EHR) comprising a plurality of multi-modal data associated with the subject, wherein the subject profile comprises a plurality of electrocardiogram (ECG) data, and wherein receiving the subject profile further comprises:

utilizing optical character recognition (OCR) to convert the EHR into machine-encoded text by pre-processing using a de-skew process at least an image of a written text; and extracting features from the EHR to reduce a dimensionality of a representation of the EHR;

identifying, using the at least one processor, contextual data as a function of the subject profile;

generating, using the at least one processor, a set of cardiac scores as a function of the contextual data and the plurality of ECG data using a set of cardiac machine learning models, wherein each cardiac score of the set of cardiac scores comprises a confidence interval indicating an accuracy of each cardiac score and wherein generating the set of cardiac scores comprises:

training a set of cardiac machine learning models, wherein:

each cardiac machine learning model of the set of cardiac machine learning models is associated with at least one stage of a plurality of stages of a coronary heart disease; and each cardiac machine learning model of the set of cardiac machine learning models is trained using cardiac training data associated with its corresponding stage of coronary heart disease; and generating at least one cardiac score of the set of cardiac scores for each cardiac machine learning model of the set of cardiac machine learning models;

selecting, using the at least one processor, one or more stages of the coronary heart disease from a plurality of stages of the coronary heart disease as a function of the set of cardiac scores and the set of confidence intervals; and displaying, using the at least one processor, a predicted diagnosis associated with the subject and through a user interface wherein the predicted diagnosis comprises the one or more stages of the coronary heart disease.

8. The method of claim 7, wherein:

generating the set of cardiac scores comprises:

iteratively training the set of cardiac machine learning models using cardiac training data, wherein the cardiac training data comprises a plurality of exemplary ECG data and a plurality of exemplary contextual data as inputs correlated to a plurality of exemplary of cardiac scores as outputs; and generating the set of cardiac scores using the trained set of cardiac machine learning models; and iteratively training the set of cardiac machine learning models comprises:

classifying the cardiac training data into a plurality of cardiac training subsets associated with the plurality of stages of the coronary heart disease; and iteratively training each cardiac machine learning model of the set of cardiac machine learning models using each cardiac training subset of the plurality of cardiac training subsets.

9. The method of claim 7, wherein the plurality of stages of the coronary heart disease comprises a plurality of ranges of total plaque volume (TPV) associated with the subject.

10. The method of claim 7, wherein the method further comprises generating, using the at least one processor, an impact score as a function of the contextual data.

11. The method of claim 10, wherein iteratively training the set of cardiac machine learning models additionally comprises calibrating each cardiac machine learning model of the set of cardiac machine learning models using the impact score.

12. The method of claim 7, wherein receiving the subject profile comprises receiving the subject profile from an electronic medical record.

* * * * *